United States Patent
Kim et al.

(10) Patent No.: US 9,738,630 B2
(45) Date of Patent: Aug. 22, 2017

(54) INHIBITORS OF LYSINE METHYL TRANSFERASE

(71) Applicant: BRISTOL-MYERS SQUIBB COMPANY, Princeton, NJ (US)

(72) Inventors: Kyoung S. Kim, Vancouver, WA (US); Liping Zhang, East Windsor, NJ (US); Ashok Vinayak Purandare, Pennington, NJ (US); Steven P. Seitz, Swarthmore, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/037,081

(22) PCT Filed: Nov. 18, 2014

(86) PCT No.: PCT/US2014/066031
§ 371 (c)(1),
(2) Date: May 17, 2016

(87) PCT Pub. No.: WO2015/077193
PCT Pub. Date: May 28, 2015

(65) Prior Publication Data
US 2016/0297806 A1   Oct. 13, 2016

Related U.S. Application Data

(60) Provisional application No. 61/905,915, filed on Nov. 19, 2013.

(51) Int. Cl.
| | |
|---|---|
| *C07D 405/12* | (2006.01) |
| *C07D 401/14* | (2006.01) |
| *C07D 413/14* | (2006.01) |
| *A61K 31/4725* | (2006.01) |
| *C07D 407/14* | (2006.01) |
| *C07D 417/14* | (2006.01) |
| *A61K 45/06* | (2006.01) |
| *A61K 31/496* | (2006.01) |
| *A61K 31/5377* | (2006.01) |
| *A61K 31/541* | (2006.01) |
| *C07D 405/14* | (2006.01) |

(52) U.S. Cl.
CPC ........ *C07D 405/12* (2013.01); *A61K 31/4725* (2013.01); *A61K 31/496* (2013.01); *A61K 31/5377* (2013.01); *A61K 31/541* (2013.01); *A61K 45/06* (2013.01); *C07D 401/14* (2013.01); *C07D 405/14* (2013.01); *C07D 407/14* (2013.01); *C07D 413/14* (2013.01); *C07D 417/14* (2013.01)

(58) Field of Classification Search
None
See application file for complete search history.

(56) References Cited

U.S. PATENT DOCUMENTS

2013/0040906 A1* 2/2013 Kuntz ................ C07D 473/34
514/46

FOREIGN PATENT DOCUMENTS

| WO | WO 2012/118812 | 9/2012 | |
|---|---|---|---|
| WO | WO 2012/142504 | 10/2012 | |
| WO | WO 2012/142513 | 10/2012 | |
| WO | WO 2013/039988 | 3/2013 | |
| WO | WO 2013/155317 | 10/2013 | |
| WO | WO 2014049488 A1 * | 4/2014 | ........... C07D 401/14 |
| WO | WO 2015/077194 | 5/2015 | |

OTHER PUBLICATIONS

Johnson, A. W. Invitation to Organic Chemistry 1999 Jones and Bartlett: Mississauga, Canada, p. 24.*
Knutson "Durable tumor regression in genetically altered malignant rhabdoid tumors by inhibition of methyltransferase EZH2." Proceedings of the National Academy of Sciences of the United States of America, 110(19), 2013, 7922-7927, S7922/1-S7922/5, Published Online Apr. 25, 2013.*

* cited by examiner

*Primary Examiner* — David K O'Dell
(74) *Attorney, Agent, or Firm* — Elliott Korsen

(57) ABSTRACT

There are disclosed compounds that are inhibitors of EZH2, pharmaceutical compositions containing said compounds and methods of treating hyperproliferative, inflammatory, infectious, and immunoregulatory disorders and diseases, utilizing the compounds of the invention.

2 Claims, No Drawings

INHIBITORS OF LYSINE METHYL TRANSFERASE

CROSS-REFERENCE TO RELATED APPLICATION

This application claims priority benefit under Title 35 §119(e) of U.S. provisional Application 61/905,915 filed Nov. 19, 2013, the contents of which are herein incorporated by reference in its entirety.

FIELD OF THE INVENTION

The present invention relates to novel compounds which are inhibitors of Enhancer of Zeste 2 (EZH2), to methods of using such compounds for inhibiting protein methyl transferases in the treatment of hyperproliferative, inflammatory, infectious, and immunoregulatory disorders and diseases, and to pharmaceutical compositions containing such compounds.

The invention also encompasses pharmaceutical compositions containing these compounds. The compounds and pharmaceutical compositions of the invention are particularly well suited as inhibitors of protein methyl transferases and consequently can be advantageously used as therapeutic agents for the treatment of, including cancer, asthma, COPD, and allergic diseases, rheumatoid arthritis, atherosclerosis, psoriasis, solid organ transplant rejection, osteoarthritis and inflammatory bowel syndrome. This invention also relates to methods of using the compounds of this invention alone or in combination with other pharmaceutically active agents.

BACKGROUND OF THE INVENTION

Cells in an organism, regardless of their function, contain identical genetic material yet vary greatly in gene expression and phenotype. Gene transcription is controlled in part through the architecture of its chromatin and through recruitment of transcription factors to specific regulatory elements. These mechanisms are regulated through covalent modifications of DNA and histone proteins that leave the underlying DNA sequence unaltered. Posttranslational modifications of histone proteins are mediated by enzymes that can add or subtract covalent attachments at specific residues. Histones can be methylated, acetylated, phosphorylated, or ubiquitinated and, depending on the residue being modified, identical chemical modifications can have opposing consequences. Histone methyl transferases (HMTs) are enzymes that catalyze the transfer of methyl groups from S-Adenosyl-L-Methionine (SAM) to specific arginine residues of proteins.

Enhancer of Zeste 2 (EZH2) is a HMT that catalyzes methylation of H3K27. Along with cofactors SUZ12, EED, and RbAp46/48, EZH2 forms the Polycomb Repressive Complex 2 (PRC2) (Morey L et al, *Trends Biochem Sci* 2010; 35 p 323-32.). EZH2 is overexpressed in a wide range of cancers, including advanced-stage and high-grade prostate, breast, and lung tumors (Albert M et. Al. *Semin Cell Dev Biol,* 2010, 21, p 209-20). EZH2 and PRC2 are critical for the control of gene expression in embryonic stem cells, maintaining self-renewal while inhibiting differentiation (Bracken A P,. *Genes Dev* 2006; 20, p 1123-36), and these properties of EZH2 appear active when the gene is overexpressed in tumors. EZH2 overexpression induces cell migration and colony formation and induces genomic instability by repression of regulators of DNA repair (Kleer C G, et al. *Proc Natl Acad Sci USA* 2003, 100, p 11606-11.). Conversely, EZH2 depletion suppresses proliferation and attenuates tumor formation in vivo (Gonzalez M E, et al., *Oncogene,* 2009, 28, p 843-53.). Recently, somatic mutations and deletions of EZH2 were identified in hematologic malignancies, leading to the gain or loss of EZH2 function. Approximately 30% of diffuse large B-cell lymphomas (DLBCL) and 10% of follicular lymphomas contain a mutation at tyrosine 641 (Y641) within the SET domain, predicted to alter the substrate recognition pocket within the enzyme (Morin R D et al., *Nat Genet,* 2010, 42, p 181-5.). These mutations are always heterozygous, suggesting that they are either dominant to or cooperate with the wild-type (WT) EZH2 protein. Enzymatic studies showed that WT EZH2 converted unmethylated H3K27 to H3K27me1 and to a lesser extent the me2 and me3 states (Sneeringer C J et al, *Proc Natl Acad Sci USA.,* 2010, 107, p 20980-5). By contrast, EZH2Y641X failed to recognize unmethylated H3K27 but readily converted H3K27me1 (created by WT EZH2) to H3K27me2 or me3. Accordingly, DLBCL cells harboring EZH2Y641X display increased levels of H3K27me3. EZH2 is silenced in resting, mature B cells and is transiently upregulated in germinal center B cells, where, along with BCL6, it blocks DNA damage response pathways allowing cells to survive the somatic hypermutation of antibody maturation (Velichutina I et al *Blood* 2010, 116, p 5247-55). By amplifying these functions and targeting additional pathways, EZH2 mutations may stimulate malignant transformation. In myeloid neoplasia, EZH2 is most often affected by deletions and nonsense mutations that yield loss of function, and leukemia cell lines harboring EZH2 mutations show decreased H3K27 methylation (Ernst T et al *Nat Genet* 2010, 42, p 722-6.). The presence of activating and inactivating EZH2 mutations in different cancers suggest a complex, context-dependent role of Polycomb proteins in oncogenesis. It is unclear whether EZH2 affects different sets of genes in different malignancies or whether global histone changes may interfere with other chromatin functions such as replication and DNA repair. Nevertheless, the frequent occurrence of genetic lesions affecting H3K27 suggests that this mark is under tight control, which may present a challenge in the design of safe and effective EZH2 inhibitors. The S-adenosylhomocysteine (SAH) hydrolase inhibitor 3-Deazaneplanocin A (DZNeP) is an early EZH2 inhibitor described (Tan J, et al. *Genes Dev* 2007, 21, p 1050-63.). DZNeP can inhibit HMTs by increasing SAH levels, inducing the degradation of EZH2 and leading to a global decrease of H3K27 methylation accompanied by apoptosis of cancer cells. However, in some cells, DZNeP decreases methylation of multiple other histone residues, perhaps as a result of the ability of SAH to compete with the AdoMet cofactor (Miranda T B et al. *Mol Cancer Ther* 2009, 8, p 1579-88.). Hence, more specific inhibitors of EZH2 are required to address various lesions in cancer. Recently inhibitors of EZH2, acting as a SAM competitor and affecting specifically the HMT activity of EZH2 (McCabe M T et al, *Nature,* 2012, 492, p 108-112.) have been reported. They also show antiproliferative activity in DLBCL cell lines expressing mutant EZH2, suggesting that direct inhibition of EZH2 activity presents a promising avenue for treatment in the clinic.

SUMMARY OF THE INVENTION

The present invention provides compounds, pharmaceutical compositions containing said compounds, and methods for treating various medical conditions using said compounds.

The present invention also provides processes and intermediates for making the compounds of the present invention or stereoisomers, tautomers or pharmaceutically acceptable salts thereof.

The present invention also provides pharmaceutical compositions comprising a pharmaceutically acceptable carrier and one or more of the compounds of the present invention or stereoisomers, tautomers or pharmaceutically acceptable salts thereof.

The compounds of the invention may be used in therapy.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

In a first aspect of the invention, there are provided compounds of formula (I)

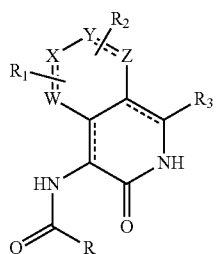

(I)

wherein
the dotted lines represent optional double bonds;
W, X, Y and Z are independently —CH— or —N—;
$R_1$ is hydrogen, halogen, $CF_3$, optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl or $C_1$-$C_6$ alkynyl, optionally substituted aryl or optionally substituted heterocyclo;
$R_2$ is hydrogen, halogen, $CF_3$, optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl or $C_1$-$C_6$ alkynyl, optionally substituted aryl or optionally substituted heterocyclo;
$R_3$ is hydrogen, halogen, $CF_3$, optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl or $C_1$-$C_6$ alkynyl, optionally substituted aryl or optionally substituted heterocyclo;
R is

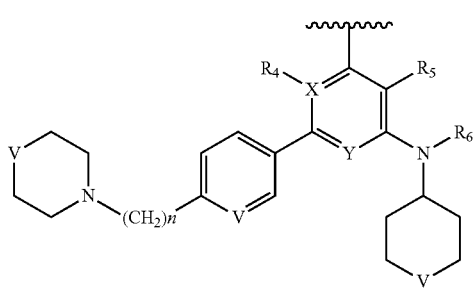

(a)

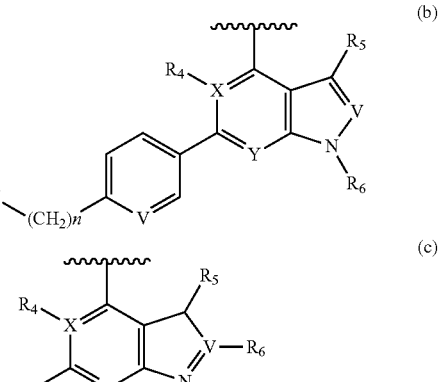

(b)

(c)

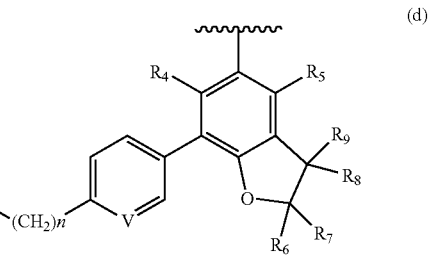

(d)

V is independently —O—, —N—, —NH—, —CH$_2$—, —SO— or SO$_2$;
$R_4$, $R_5$, $R_6$, $R_7$, $R_8$ and $R_9$ are independently hydrogen, halogen, $CF_3$, optionally substituted $C_1$-$C_6$ alkyl, optionally substituted $C_3$-$C_8$ cycloalkyl, $C_1$-$C_6$ alkenyl, $C_1$-$C_6$ alkynyl, optionally substituted aryl or optionally substituted heterocyclo; or
$R_7$ and $R_8$ may be taken together to form a fused $C_3$-$C_8$ cycloalkyl group,
$R_6$ and $R_7$ may be taken together to form a spiro $C_3$-$C_8$ cycloalkyl group; or
$R_8$ and $R_9$ may be taken together to form a spiro $C_3$-$C_8$ cycloalkyl group;
n is 0, 1 or 2;
or a pharmaceutically acceptable salt, tautomer or stereoisomer thereof.

In a second aspect of the invention, there are provided compounds of formula II

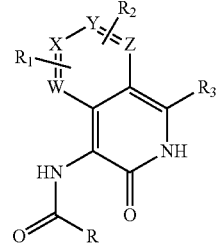

(II)

wherein
W, X, Y and Z are independently —CH— or —N—;
$R_1$ is hydrogen, halogen, $CF_3$, optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl or $C_1$-$C_6$ alkynyl, optionally substituted aryl or optionally substituted heterocyclo;

R$_2$ is hydrogen, halogen, CF$_3$, optionally substituted C$_1$-C$_6$ alkyl, optionally substituted C$_1$-C$_6$ alkoxy, optionally substituted C$_3$-C$_8$ cycloalkyl, C$_1$-C$_6$ alkenyl or C$_1$-C$_6$ alkynyl, optionally substituted aryl or optionally substituted heterocyclo;

R$_3$ is hydrogen, halogen, CF$_3$, optionally substituted C$_1$-C$_6$ alkyl, optionally substituted C$_1$-C$_6$ alkoxy, optionally substituted C$_3$-C$_8$ cycloalkyl, C$_1$-C$_6$ alkenyl or C$_1$-C$_6$ alkynyl, optionally substituted aryl or optionally substituted heterocyclo;

R is

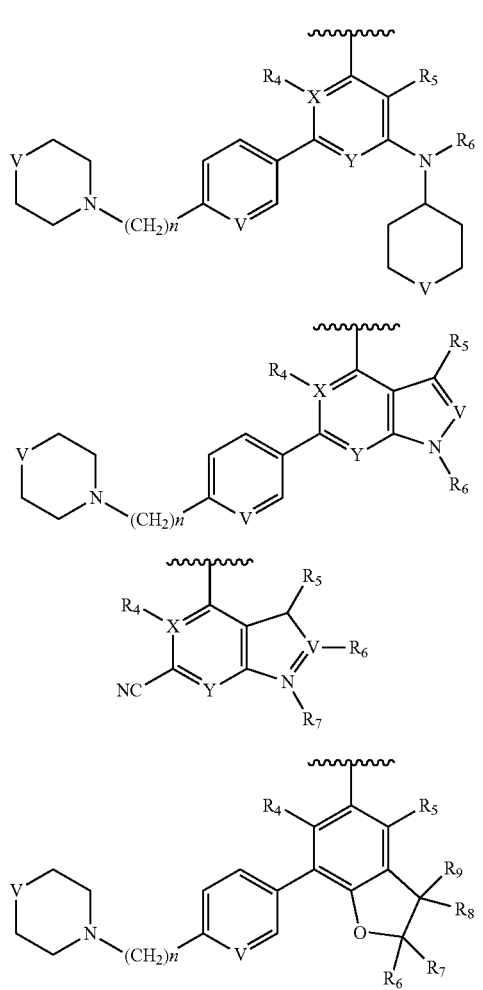

V is independently —O—, —N—, —NH—, —CH$_2$—, —SO— or SO$_2$;

R$_4$, R$_5$, R$_6$, R$_7$, R$_8$ and R$_9$ are independently hydrogen, halogen, CF$_3$, optionally substituted C$_1$-C$_6$ alkyl, optionally substituted C$_3$-C$_8$ cycloalkyl, C$_1$-C$_6$ alkenyl, C$_1$-C$_6$ alkynyl, optionally substituted aryl or optionally substituted heterocyclo; or R$_7$ and R$_8$ may be taken together to form a fused C$_3$-C$_8$ cycloalkyl group, R$_6$ and R$_7$ may be taken together to form a spiro C$_3$-C$_8$ cycloalkyl group; or R$_8$ and R$_9$ may be taken together to form a spiro C$_3$-C$_8$ cycloalkyl group;

n is 0, 1 or 2;

or a pharmaceutically acceptable salt, tautomer or stereoisomer thereof.

In a third aspect within the first and second aspects, there are provided compounds of the invention wherein W, X, Y and Z are independently —CH—;

R$_1$ is hydrogen, halogen, CF$_3$, optionally substituted C$_1$-C$_6$ alkyl, optionally substituted C$_1$-C$_6$ alkoxy or optionally substituted C$_3$-C$_8$ cycloalkyl;

R$_2$ is hydrogen, halogen, CF$_3$, optionally substituted C$_1$-C$_6$ alkyl, optionally substituted C$_1$-C$_6$ alkoxy or optionally substituted C$_3$-C$_8$ cycloalkyl;

R$_3$ hydrogen, halogen, CF$_3$, optionally substituted C$_1$-C$_6$ alkyl, optionally substituted C$_1$-C$_6$ alkoxy or optionally substituted C$_3$-C$_8$ cycloalkyl;

R is

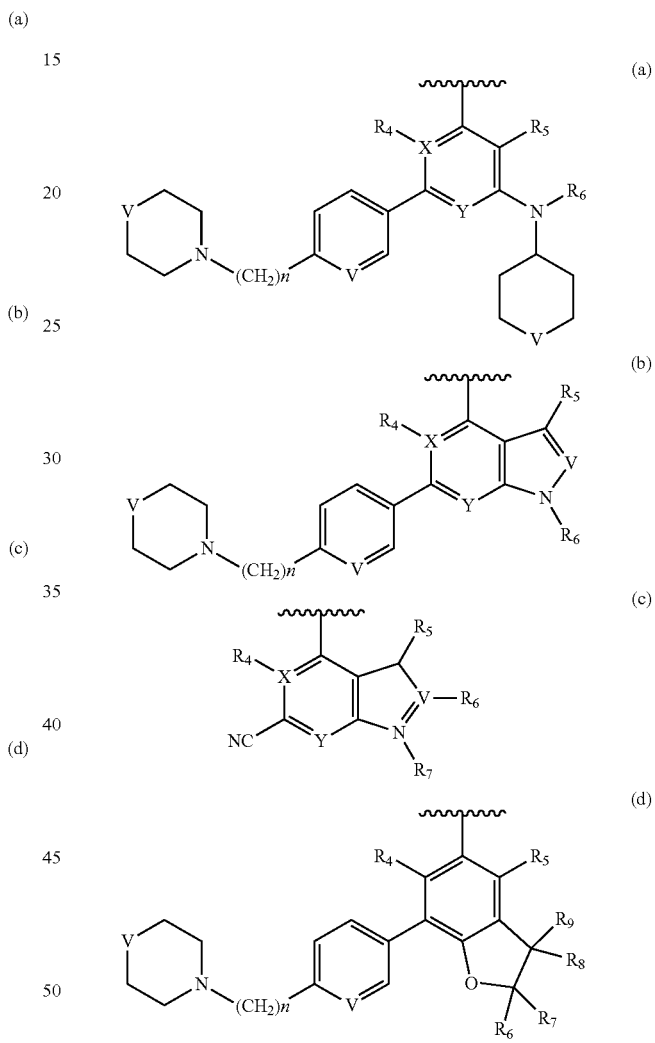

V is independently —O—, —N—, —NH—, —CH$_2$—, —SO— or SO$_2$;

R$_4$, R$_5$, R$_6$, R$_7$, R$_8$ and R$_9$ are independently hydrogen, halogen, CF$_3$, optionally substituted C$_1$-C$_6$ alkyl or optionally substituted C$_3$-C$_8$ cycloalkyl; or R$_7$ and R$_8$ may be taken together to form a fused C$_3$-C$_8$ cycloalkyl group, R$_6$ and R$_7$ may be taken together to form a spiro C$_3$-C$_8$ cycloalkyl group; or R$_8$ and R$_9$ may be taken together to form a spiro C$_3$-C$_8$ cycloalkyl group;

n is 0, 1 or 2;

or a pharmaceutically acceptable salt, tautomer or stereoisomer thereof.

In a fourth aspect within the first and second aspects, there are provided compounds of the invention wherein W, X, Y and Z are independently —CH— or —N—;

$R_1$ is hydrogen, halogen, $CF_3$, optionally substituted $C_1$-$C_6$ alkyl, optionally substituted $C_1$-$C_6$ alkoxy or optionally substituted $C_3$-$C_8$ cycloalkyl;

$R_2$ is hydrogen, halogen, $CF_3$, optionally substituted $C_1$-$C_6$ alkyl, optionally substituted $C_1$-$C_6$ alkoxy or optionally substituted $C_3$-$C_8$ cycloalkyl;

$R_3$ hydrogen, halogen, $CF_3$, optionally substituted $C_1$-$C_6$ alkyl, optionally substituted $C_1$-$C_6$ alkoxy or optionally substituted $C_3$-$C_8$ cycloalkyl;

R is

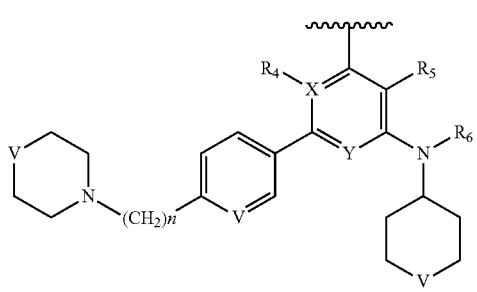

(a)

V is independently —O—, —N—, —NH—, —CH$_2$—, —SO— or SO$_2$;

$R_4$, $R_5$ and $R_6$ are independently hydrogen, halogen, $CF_3$, optionally substituted $C_1$-$C_6$ alkyl or optionally substituted $C_3$-$C_8$ cycloalkyl; or n is 0, 1 or 2;

or a pharmaceutically acceptable salt, tautomer or stereoisomer thereof.

In a fifth aspect within the prior aspects, there are provided compounds of the invention wherein W, X, Y and Z are independently —CH— or —N—;

$R_1$ is hydrogen, halogen, $CF_3$, optionally substituted $C_1$-$C_6$ alkyl, optionally substituted $C_1$-$C_6$ alkoxy or optionally substituted $C_3$-$C_8$ cycloalkyl;

$R_2$ is hydrogen, halogen, $CF_3$, optionally substituted $C_1$-$C_6$ alkyl, optionally substituted $C_1$-$C_6$ alkoxy or optionally substituted $C_3$-$C_8$ cycloalkyl;

$R_3$ hydrogen, halogen, $CF_3$, optionally substituted $C_1$-$C_6$ alkyl, optionally substituted $C_1$-$C_6$ alkoxy or optionally substituted $C_3$-$C_8$ cycloalkyl;

R is

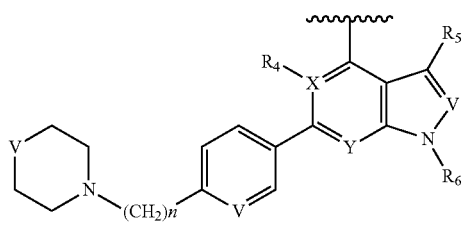

(b)

V is independently —O—, —N—, —NH—, —CH$_2$—, —SO— or SO$_2$;

$R_4$, $R_5$ and $R_6$ are independently hydrogen, halogen, $CF_3$, optionally substituted $C_1$-$C_6$ alkyl or optionally substituted $C_3$-$C_8$ cycloalkyl; or n is 0, 1 or 2;

or a pharmaceutically acceptable salt, tautomer or stereoisomer thereof.

In a sixth aspect within the first and second aspects, there are provided compounds of the invention wherein within the prior aspects, there are provided compounds of the invention wherein W, X, Y and Z are independently —CH— or —N—;

$R_1$ is hydrogen, halogen, $CF_3$, optionally substituted $C_1$-$C_6$ alkyl, optionally substituted $C_1$-$C_6$ alkoxy or optionally substituted $C_3$-$C_8$ cycloalkyl;

$R_2$ is hydrogen, halogen, $CF_3$, optionally substituted $C_1$-$C_6$ alkyl, optionally substituted $C_1$-$C_6$ alkoxy or optionally substituted $C_3$-$C_8$ cycloalkyl;

$R_3$ hydrogen, halogen, $CF_3$, optionally substituted $C_1$-$C_6$ alkyl, optionally substituted $C_1$-$C_6$ alkoxy or optionally substituted $C_3$-$C_8$ cycloalkyl;

R is

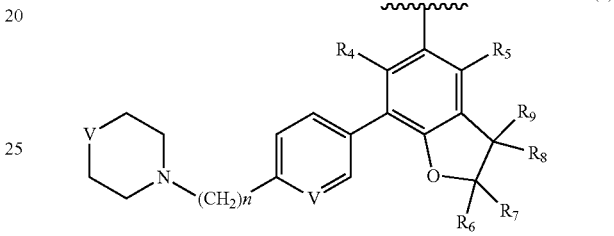

(d)

V is independently —O—, —N—, —NH—, —CH$_2$—, —SO— or SO$_2$;

$R_4$, $R_5$, $R_6$, $R_7$, $R_8$ and $R_9$ are independently hydrogen, halogen, $CF_3$, optionally substituted $C_1$-$C_6$ alkyl or optionally substituted $C_3$-$C_8$ cycloalkyl; or $R_7$ and $R_8$ may be taken together to form a fused $C_3$-$C_8$ cycloalkyl group, $R_6$ and $R_7$ may be taken together to form a spiro $C_3$-$C_8$ cycloalkyl group; or $R_8$ and $R_9$ may be taken together to form a spiro $C_3$-$C_8$ cycloalkyl group;

n is 0, 1 or 2;

or a pharmaceutically acceptable salt, tautomer or stereoisomer thereof.

In another aspect, the invention provides a compound selected from the exemplified examples within the scope of the first aspect, or a pharmaceutically acceptable salt, tautomer or stereoisomer thereof.

In another aspect, the invention provides a compound selected from any subset list of compounds within the scope of any of the above aspects.

In another aspect, the invention provides a compound selected from the following 5-(Ethyl (tetrahydro-2H-pyran-4-yl)amino)-4-methyl-N-((1-methyl-3-oxo-2,3-dihydroisoquinolin-4-yl)methyl)-4'-(morpholinomethyl)-[1,1'-biphenyl]-3-carboxamide, 5-(Ethyl(tetrahydro-2H-pyran-4-yl)amino)-N-((7-fluoro-1-methyl-3-oxo-2,3-dihydroisoquinolin-4-yl)methyl)-4-methyl-4'-(morpholinomethyl)-[1,1'-biphenyl]-3-carboxamide, N-((6,7-Dimethoxy-1-methyl-3-oxo-2,3-dihydroisoquinolin-4-yl)methyl)-5-(ethyl(tetrahydro-2H-pyran-4-yl)amino)-4-methyl-4'-(morpholinomethyl)-[1,1'-biphenyl]-3-carboxamide, 5-(Ethyl (tetrahydro-2H-pyran-4-yl)amino)-N-((6-methoxy-1-methyl-3-oxo-2,3-dihydroisoquinolin-4-yl)methyl)-4-methyl-4'-(morpholinomethyl)-[1,1'-biphenyl]-3-carboxamide, 5-(Ethyl (tetrahydro-2H-pyran-4-yl)amino)-N-((5-fluoro-1-methyl-3-oxo-1,2,3,4-tetrahydroisoquinolin-4-yl)methyl)-4-methyl-4'-(morpholinomethyl)-[1,1'-biphenyl]-3-carboxamide, 5-(Ethyl (tetrahydro-2H-pyran-4-yl)amino)-N-((5-fluoro-1-methyl-3-oxo-2,3-dihydroisoquinolin-4-yl)methyl)-4-methyl-4'-(morpholinomethyl)-[1,1'-biphenyl]-3-carboxamide, 5-(Ethyl (tetrahydro-2H-pyran-4-yl)amino)-4-methyl-N-((1-methyl-3-oxo-2,3,5,6,7,8-hexahydroisoquinolin-4-yl)methyl)-4'-(morpholinomethyl)-[1,1'-biphenyl]-3-carboxamide, 4'-((1,1-Dioxidothiomorpholino)methyl)-5-(ethyl(tetrahydro-2H-pyran-4-yl)amino)-4-methyl-N-((1-methyl-3-oxo-2,3,5,6,7,8-hexahydroisoquinolin-4-yl)methyl)-[1,1'-biphenyl]-3-carboxamide, tert-Butyl 4-(5-(1-(sec-butyl)-3-methyl-4-(((1-methyl-3-oxo-2,3-dihydroisoquinolin-4-yl)methyl)carbamoyl)-1H-indol-6-yl)pyridin-2-yl)piperazine-1-carboxylate, 1-(sec-Butyl)-3-methyl-N-((1-methyl-3-oxo-2,3-dihydroisoquinolin-4-yl)methyl)-6-(6-(piperazin-1-yl)pyridin-3-yl)-1H-indole-4-carboxamide, N-((6,8-Difluoro-1-methyl-3-oxo-2,3-dihydroisoquinolin-4-yl)methyl)-5-(ethyl(tetrahydro-2H-pyran-4-yl)amino)-4-methyl-4'-(morpholinomethyl)-[1,1'-biphenyl]-3-carboxamide, 5-(Ethy (tetrahydro-2H-pyran-4-yl)amino)-N-((8-fluoro-1-methyl-3-oxo-2,3-dihydroisoquinolin-4-yl)methyl)-4-methyl-4'-(morpholinomethyl)-[1,1'-biphenyl]-3-carboxamide, 5-(Ethyl (tetrahydro-2H-pyran-4-yl)amino)-4-methyl-N-((1-methyl-3-oxo-7-(trifluoromethyl)-2,3-dihydroisoquinolin-4-yl)methyl)-4'-(morpholinomethyl)-[1,1'-biphenyl]-3-carboxamide, 5-(Ethyl (tetrahydro-2H-pyran-4-yl)amino)-N-((1-ethyl-3-oxo-2,3-dihydroisoquinolin-4-yl)methyl)-4-methyl-4'-(morpholinomethyl)-[1,1'-biphenyl]-3-carboxamide, 5-(Ethyl (tetrahydro-2H-pyran-4-yl)amino)-N-((1-ethyl-7-fluoro-3-oxo-2,3-dihydroisoquinolin-4-yl)methyl)-4-methyl-4'-(morpholinomethyl)-[1,1'-biphenyl]-3-carboxamide, N-((1,7-Dimethyl-3-oxo-2,3-dihydroisoquinolin-4-yl)methyl)-5-(ethyl(tetrahydro-2H-pyran-4-yl)amino)-4-methyl-4'-(morpholinomethyl)-[1,1'-biphenyl]-3-carboxamide, 2,2-Dimethyl-N-((1-methyl-3-oxo-2,3-dihydroisoquinolin-4-yl)methyl)-7-(6-(piperazin-1-yl)pyridin-3-yl)-2,3-dihydrobenzofuran-5-carboxamide, or a pharmaceutically acceptable salt, tautomer or stereoisomer thereof.

In one embodiment, the compounds of the invention have $IC_{50}$ values≤5.0 µM.

In another embodiment, the compounds of the invention have $IC_{50}$ values≤0.5 µM.

In another embodiment, the compounds of the invention have $IC_{50}$ values≤0.05 µM.

II. Other Embodiments of the Invention

In another embodiment, the present invention provides a composition comprising one or more compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a method for the treatment and/or prophylaxis of various types of cancer, comprising administering to a patient in need of such treatment and/or prophylaxis a therapeutically effective amount of one or more compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with the inhibition of apoptosis.

In another aspect, the invention provides a method of treating a patient suffering from or susceptible to a medical condition that is sensitive to apoptosis. A number of medical conditions can be treated. The method comprises administering to the patient a therapeutically effective amount of a composition comprising a compound described herein. For example, the compounds described herein may be used to treat or prevent infections, proliferative diseases (e.g., cancer), and autoimmune diseases.

In another aspect, the invention provides a method of inhibiting the activity of an IAP in a cell, thus promoting apoptosis. The method comprises exposing the cell to a compound described herein.

III. Therapeutic Applications

The compounds and pharmaceutical compositions of the present invention are useful in treating or preventing any disease or conditions that are sensitive to apoptosis. These include infections (e.g. skin infections, GI infection, urinary tract infections, genito-urinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the animal. In certain embodiments, the compound or pharmaceutical composition is administered orally. In other embodiments, the compound or pharmaceutical composition is administered parenterally.

In one embodiment, the compounds of this invention can be used for the treatment of any cancer type that fails to undergo apoptosis in a patient. This includes, but is not limited to: solid tumors, including but not limited to carcinomas; sarcomas including Kaposi's sarcoma; erythroblastoma; glioblastoma; meningioma; astrocytoma; melanoma;

and myoblastoma. Treatment or prevention of non-solid tumor cancers, such as leukemia, is also contemplated by this invention.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjogren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

Compounds of the invention are useful for sensitizing cells to apoptotic signals. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

IV. Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

V. Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (—) that is not between two letters or symbols; this is used to indicate a point of attachment for a substituent. For example, —CONH$_2$ is attached through the carbon atom.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "$C_2$-$C_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

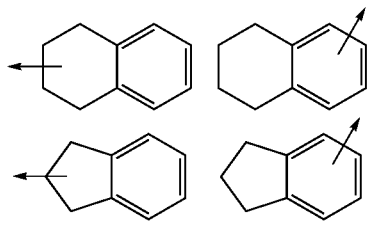

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the carbazole core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the carbazole core of the compound.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (NO) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). Prodrugs and Targeted Delivery (*Methods and Principles in Medicinal Chemistry*), Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared by methods such as those illustrated in the following schemes and examples utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

Examples 1 and 2 were prepared following the procedure shown in Scheme 1.

Selective bromination of 1-methylisoquinolin-3(2H)-one (prepared following the literature procedure, US patent 2009/0197862 A1, page 19) using cyanogen bromide provided 4-bromoisoquinolne derivative. Metallation of the bromo compound followed by reacting with DMF provided the aldehyde compound. Reductive alkylation of the aldehyde with tert-butyl carbamate (ref: *Tet Lett,* 1999, 40, 2295-2298) followed by deprotection and couping with 5-(ethyl(tetrahydro-2H-pyran-4-yl)amino)-4-methyl-4'-(morpholinomethyl)[1,1'-biphenyl]-3-carboxylic acid (ref: WO 2012/142504) provided Examples 1 (X=H) and 2 (X=F).

Scheme 1
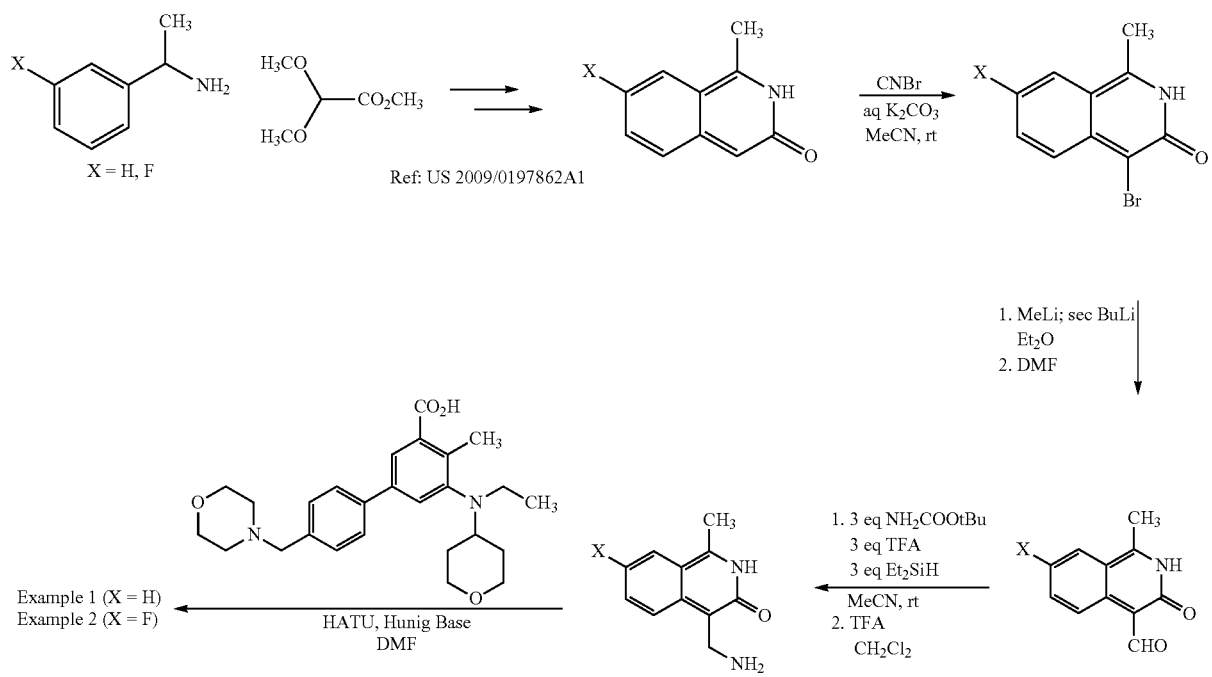
Example 3 and 4 were prepared following the Scheme 2.
Compound 6,7-dimethoxy-1-methylisoquinolin-3(2H)-one (ref: PCT/US 2012/025731) was brominated selectively at C-4 using cyanogen bromide. The bromo compound was converted to the final product following the similar procedure as shown in Scheme 1.
Scheme 2
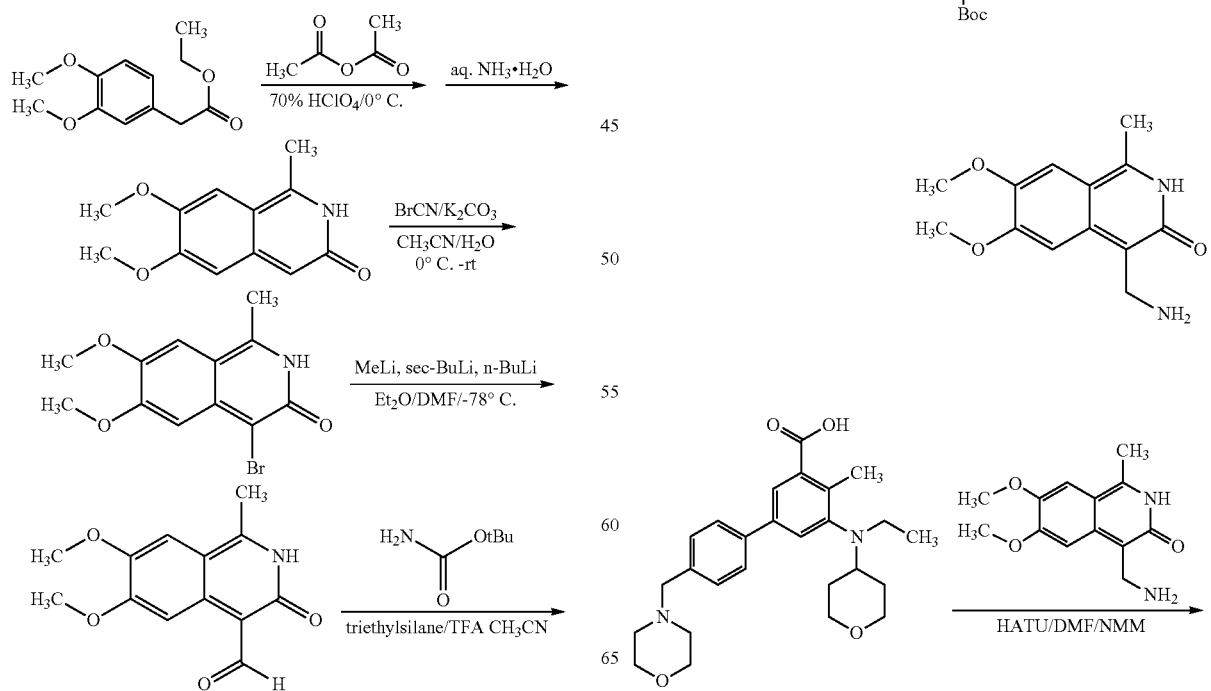
-continued
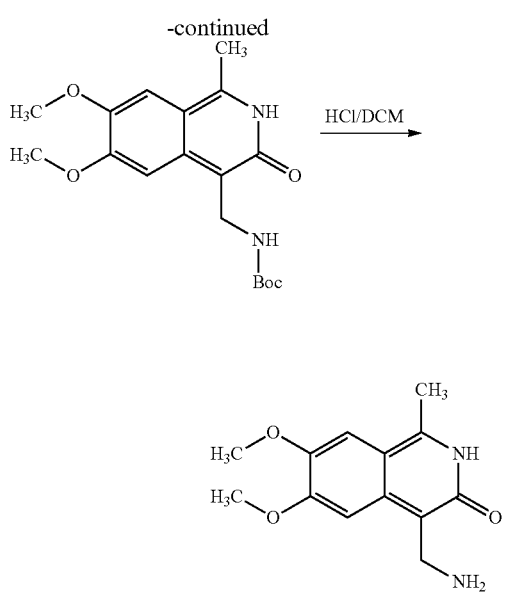

27

-continued

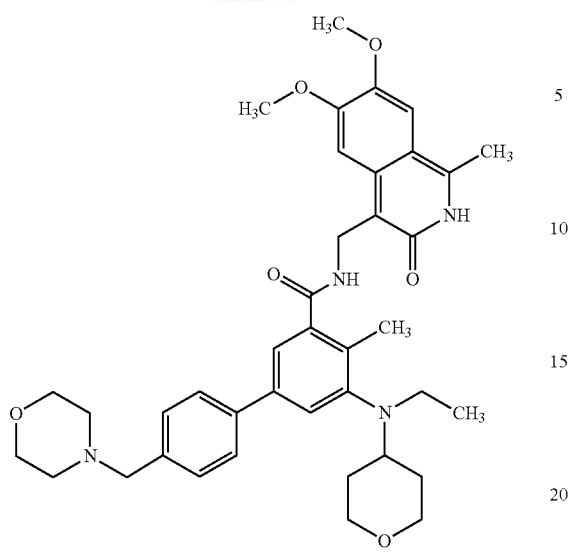

Examples 5 and 6 were prepared following the similar procedure as shown in Scheme 3.

Condensation of 1-(2,3-difluorophenyl)ethanone and 2-cyanoacetamide in the presence of base provided 5-fluoro-1-methyl-3-oxo-2,3-dihydroisoquinoline-4-carbonitrile. Hydrogenation followed by coupling with the acid and oxidation in the presence of NaH (ref: *J. Heterocyclic Chem.*, 1982, 19, 49-53) provided Example 6.

Scheme 3

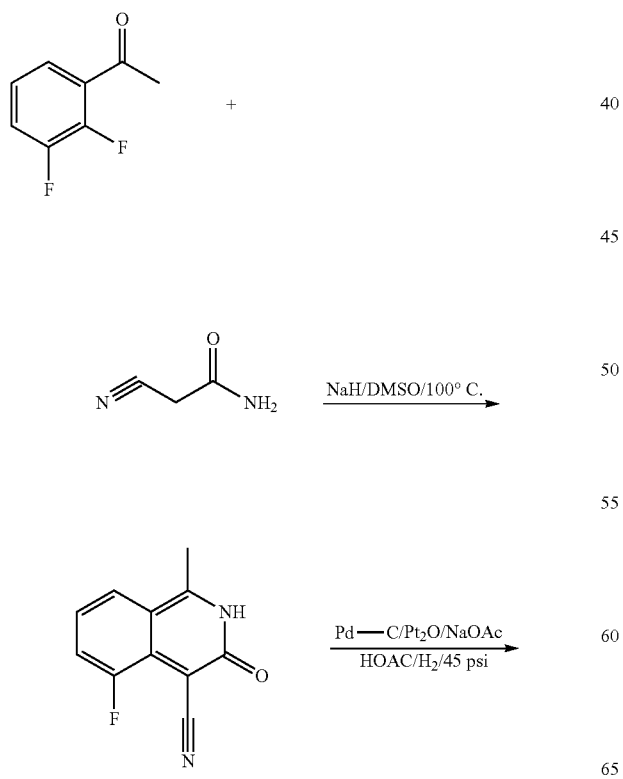

28

-continued

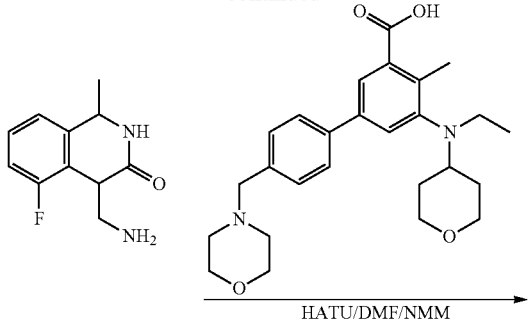

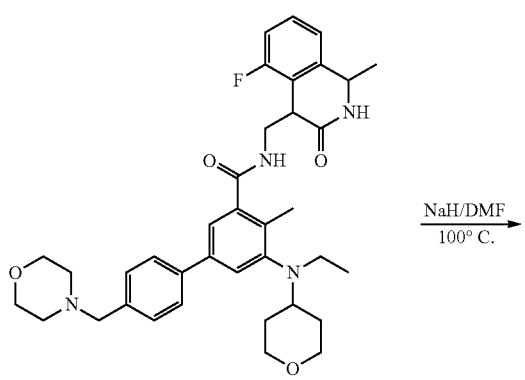

Example 5

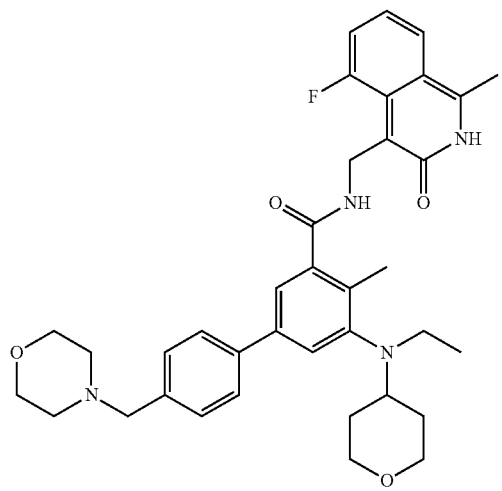

Example 6

Example 8 was prepared following a similar procedure as shown in Scheme 4.

Scheme 4
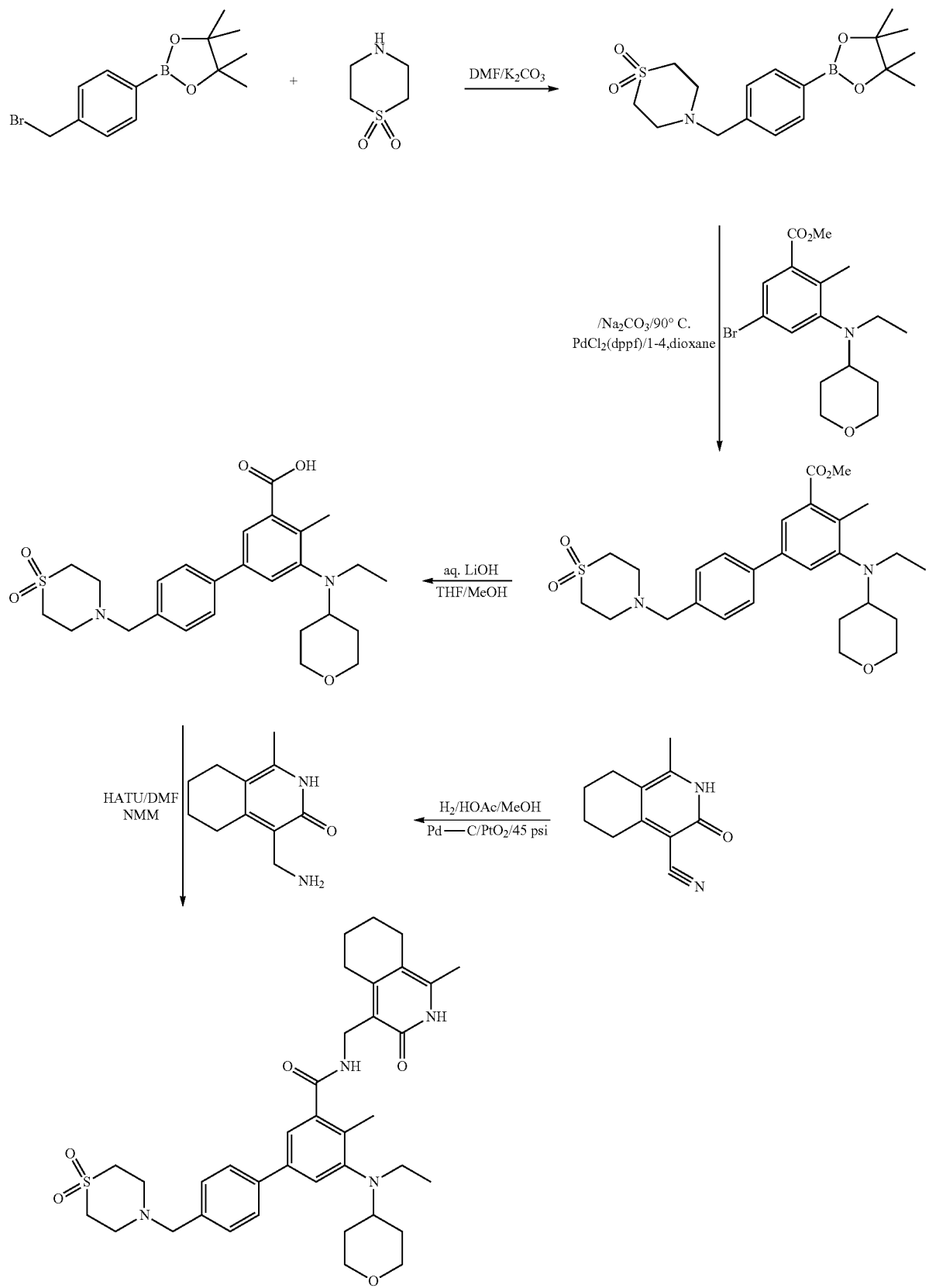

Trifluoromethyl Substituted isoquinolone Analog Example 13 was Prepared as Shown in Scheme 5.

Isoquinolone intermediate was methylated using trimethyloxonium tetrafluoroborate to give 3-methoxyisoquinoline. Reduction of the cyano group followed by coupling with the acid and demethylation using HBr/HOAc provided the final compound.

F254 were used with visualization by UV light at 254 nM, exposure to iodine vapor, or heating with PMA (phosphomolybdic acid solution), ninhydrin in ethanol, anisaldehyde solution, or ceric ammonium molybdate solution.

Unless otherwise specified, "dried" refers to the addition of anhydrous MgSO$_4$ followed by filtration and rinsing the residual solids with an appropriate organic solvent.

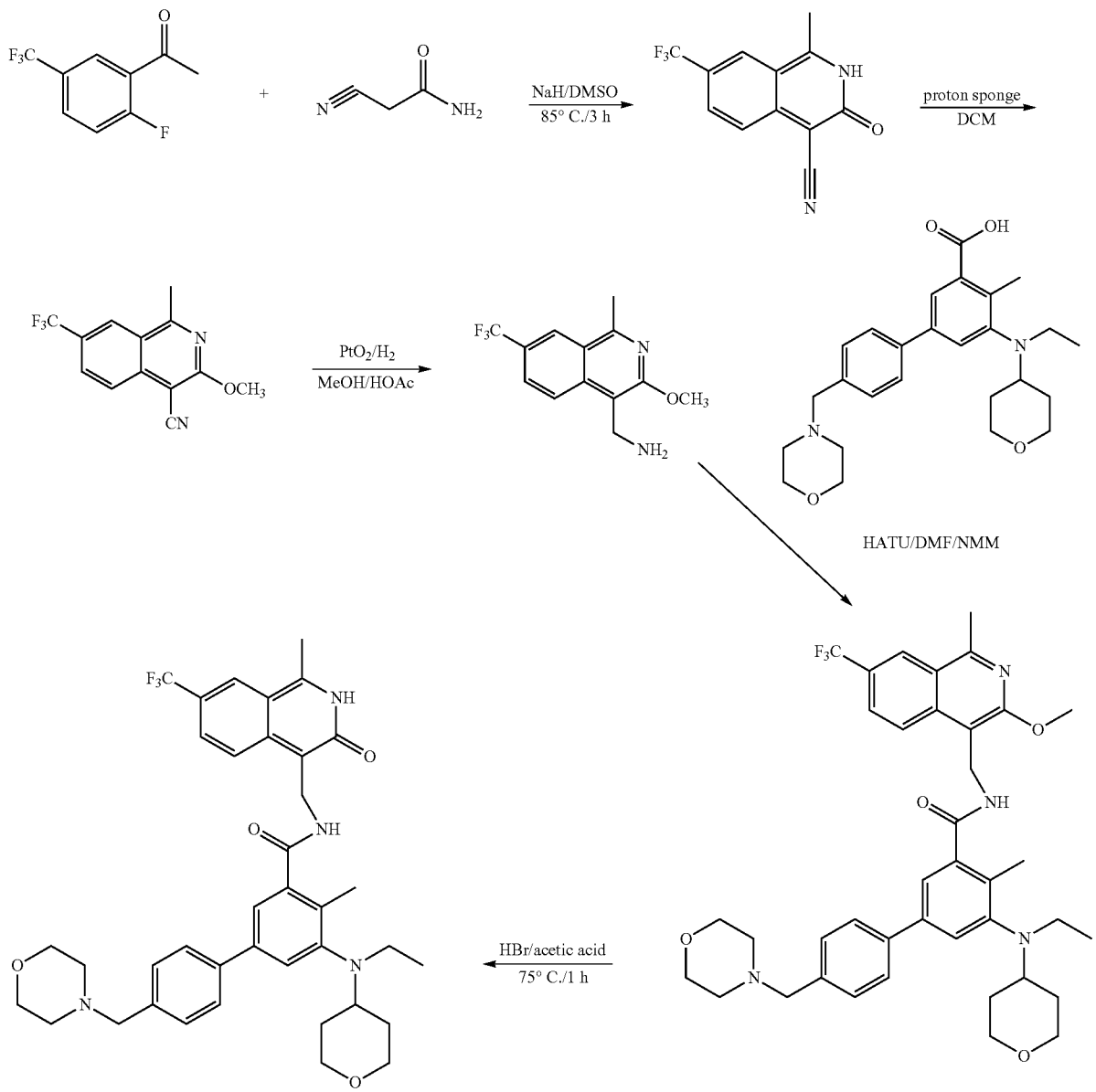

Scheme 5

GENERAL EXPERIMENTAL

Air- or moisture-sensitive reactions were generally performed under an atmosphere of nitrogen or argon in anhydrous solvents (EMD DRISOLV®). Reaction concentrations are given in units of molar and are approximate. Temperatures are given in degrees Celsius. Reactions were monitored for completeness by thin layer chromatography (TLC) or tandem liquid chromatography-mass spectroscopy (LCMS). For TLC, 0.25 mm plates coated with Silica60/

"Stripped" means concentration under reduced pressure, generally on a rotary evaporator. "Silica gel chromatography", "flash chromatography", or "chromatographed on silica gel" refers to glass column chromatography performed in a manner similar to that described by Still (*J. Org. Chem.*, 43:2923 (1978)). Typically silica gel 60 (EMD, 230-400 mesh ASTM) is used with solvents from JT Baker or Mallinckrodt. HPLC refers to purification by reverse-phase high-performance liquid chromatography generally on C18 columns using the stated mobile phases. Analytical HPLC runs were performed using the columns, flow rates, and mobile phases indicated. It is understood that analytical HPLC retention times ($T_r$) are reported in minutes, and may be dependent on temperature, pH, and other factors. ISCO refers to chromatography on pre-packed silica gel cartridges using automated systems marketed by Teledyne Isco. For all chromatographic purifications the isolation of product by concentration of the appropriate fractions by evaporation at or below ambient pressure is implied. Melting points were determined on a Thomas-Hoover Uni-Melt apparatus and are uncorrected. Generally, mass spectral results are reported as the $(M+H)^+$ value. For halogenated compounds where two or more peaks are significant, m/z for one peak in the cluster, generally the most intense, is reported. $^1$H NMR spectra were recorded on dilute solutions at 400 or 500 MHz on Bruker® instruments in the solvents indicated. Chemical shifts are reported in parts per million (ppm) downfield from internal tetramethylsilane (TMS) or from the position of TMS inferred by the deuterated NMR solvent. Apparent multiplicities are reported as: singlet-s, doublet-d, triplet-t, quartet-q, or multiplet-m. Peaks which exhibit broadening are further denoted as br. Integrations are approximate. It should be noted that integration intensities, peak shapes, chemical shifts and coupling constants can be dependent on solvent, concentration, temperature, pH, and other factors. Further, peaks which overlap with or exchange with water or solvent peaks in the NMR spectrum may not provide reliable integration intensities.

Unless otherwise specified, the various substituents of the compounds as employed herein are defined in the same manner as compounds of the invention of Formula (I).

For ease of reference, the following abbreviations are used herein.

Abbreviations

| | |
|---|---|
| AcOH, HOAc | acetic acid |
| ACN | acetonitrile |
| Ac$_2$O | acetic anhydride |
| ADDP | 1,1'-(azodicarbonyl)dipiperidine |
| aq. | aqueous |
| Bn | benzyl |
| Boc | t-butyl carbamate |
| Boc$_2$O | di-t-butyl dicarbonate |
| BOP | Benzotriazol-1-yloxytris(dimethylamino)phosphonium hexafluorophosphate |
| Bu | butyl |
| Cbz | benzyl carbamate |
| conc. | concentrated |
| DCE | 1,2-dichloroethane |
| DCM | dichloromethane |
| DIAD | diisopropyl azodicarboxylate |
| DIEA | N,N-diisopropylethylamine |
| DMAP | 4-N,N-dimethylaminopyridine |
| DMF | dimethylformamide |
| DMSO | dimethylsulfoxide |
| DMT-MM | 4-(4,6-dimethoxy-1,3,5-triazin-2-yl)-4-methylmorpholinium chloride |
| EDC | 1-(3-(dimethylamino)propyl)-3-ethylcarbodiimide hydrochloride |
| Et | ethyl |
| EtOAc | ethyl acetate |
| EtOH | ethanol |
| Et$_2$O | diethyl ether |
| Et$_3$N | triethylamine |
| Fmoc | 9-fluorenylmethyl carbamate |
| h | hour(s) |
| HATU | O-(7-azabenzotriazol-1-yl)-N,N,N',N'-tetramethyluronium hexafluorophosphate |
| HOAt | 1-hydroxy-7-azabenzotriazole |
| HPLC | high performance liquid chromatography |
| i-PrOH | isopropanol |
| KOAc | potassium acetate |
| LAH | Lithium aluminum hydride |
| min | minute(s) |
| Me | methyl |
| MeCN | acetonitrile |
| MeOH | methanol |
| Me$_2$NH | dimethylamine |
| NaHMDS | sodium bis(trimethylsilyl)amide |
| Na(OAc)$_3$BH | sodium triacetoxyborohydride |
| n-BuLi | n-butyllithium |
| NCS | N-chlorosuccinimide |
| NMM | N-methylmorpholine |
| NMP | n-methylpyrrolidinone |
| NMR | nuclear magnetic resonance |
| OTf | trifluoromethylsulfonyloxy |
| Pd/C | palladium on carbon |
| Pd(dppf)$_2$Cl$_2$ | [1,1'-bis(diphenylphosphino)ferrocene]dichloropalladium(II) |
| Pd(OAc)$_2$ | palladium acetate |
| Pd(PPh$_3$)$_4$ | tetrakis(triphenylphosphine)palladium |
| Pd$_2$(dba)$_3$ | tris(dibenzylideneacetone)dipalladium(0) |
| PE | Petroleum ether |
| Ph | phenyl |
| PhMe | toluene |
| Ph$_2$TfN | 1,1,1-trifluoro-N-phenyl-N-(trifluoromethyl)sulfonyl methanesulfonamide |
| PPh$_3$ | triphenylphosphine |
| RB | Round-bottom flask |
| rt | room temperature |
| RCM | Ring-closing metathesis |
| sat. | saturated |
| t-Bu | tertiary butyl |
| t-BuOH | tertiary butanol |
| TFA | trifluoroacetic acid |
| Tf$_2$O | trifluoromethylsulfonic anhydride |
| THF | tetrahydrofuran |
| TMS | trimethylsilyl |
| TsO | p-toluenesulfonyl |

Example 1

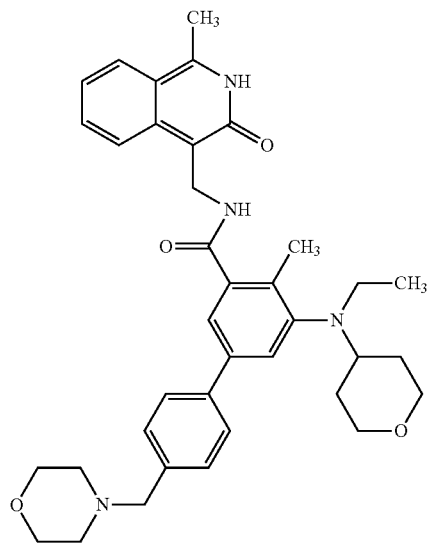 [SMILES: CCN(c1cc(-c2ccc(CN3CCOCC3)cc2)cc(C(=O)NCc2c(=O)[nH]c(C)c3ccccc23)c1C)C1CCOCC1]

5-(Ethyl(tetrahydro-2H-pyran-4-yl)amino)-4-methyl-N-((1-methyl-3-oxo-2,3-dihydroisoquinolin-4-yl)methyl)-4'-(morpholinomethyl)-[1,1'-biphenyl]-3-carboxamide

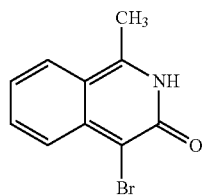

A) 4-Bromo-1-methylisoquinoline-3(2H)-one

To a heterogeneous mixture of 1-methylisoquinolin-3(2H)-one (4.35 g, 27.3 mmol) in MeCN (50 mL) and $K_2CO_3$ (4.53 g) in $H_2O$ (25 mL) at rt was added a solid of cyanic bromide (3.47 g, 32.8 mmol) with stirring. After 45 min at rt 5 mL of water (5 mL) was added to the reaction mixture to make it more stirrable. After 70 min at rt additional CNBr (1 g) was added and the mixture was stirred overnight at rt. Next morning the precipitated solid was filtered, washed with a small amount of water and dried to obtain 2.74 g of the desired product as a yellow solid. To the filtrate solution was added 6 N HCl (3 mL) and EtOAc (120 mL). The organic layer was separated, dried over $MgSO_4$, and concentrated in vacuo to obtain ~2 g of the mixture of products. This material was purified by flash column on silica gel eluting with $CH_2Cl_2$/MeOH gradient system to obtain 0.40 g of the desired product, total 3.14 g (48%). $^1$H NMR ($CDCl_3$) δ 8.13 (d, J=8.8 Hz, 1 H), 8.01 (d, J=8.6 Hz, 1 H), 7.80 (m, 1 H), 7.45 (m, 1 H), 3.03 (s, 3 H); MS(ESI$^+$) m/z 238.1, 240.1 (M+H)$^+$.

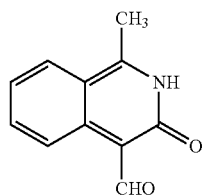

B) 1-Methyl-3-oxo-2,3-dihydroisoquinoline-4-carbaldehyde

To a heterogeneous mixture of 4-bromo-1-methylisoquinolin-3(2H)-one (238 mg, 1.000 mmol) in anhydrous $Et_2O$ (5 mL) at −78° C. under $N_2$ atm was added 0.5 mL of 3 M MeLi solution in DME and it was stirred for 20 min. Here was added 1.2 mL of 1.4 M sec-BuLi in cyclohexane at −78° C., stirred for 35 min, and was added 0.8 mL of DMF at −78° C. The reaction mixture was stirred for 1.5 h at −78° C. To the reaction mixture were added 5 mL of 1.5 M $K_2HPO_4$, 25 mL $H_2O$ and EtOAc (50 mL), and EOAc layer was separated. This EtOAc layer contained very little desired product and it was discarded. Aq HCl was added to the aqueous layer adjusting its pH to around zero and it was concentrated to a volume of ~10 mL. The yellow precipitates was filtered, washed with a small amount of water to obtain the desired product (50 mg, crude yield 27%) which was slightly impure. This material was used directly for the next step without any further purification.

$^1$H NMR (DMSO-d$_6$) δ 10.38 (s, 1 H), 9.07 (d, J=8.8 Hz, 1 H), 8.04 (d, J=8.6 Hz, 1 H), 7.72 (m, 1 H), 7.25 (m, 1 H), 2.88 (s, 3 H); MS(ESI$^+$) m/z 188.2 (M+H)$^+$.

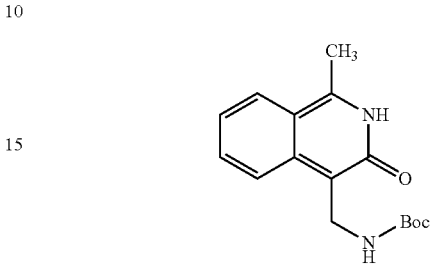

C) tert-Butyl ((1-methyl-3-oxo-2,3-dihydroisoquinolin-4-yl)methyl)carbamate

A mixture of 1-methyl-3-oxo-2,3-dihydroisoquinoline-4-carbaldehyde (40 mg, 0.214 mmol), tert-butyl carbamate (75 mg, 0.641 mmol), triethylsilane (74.5 mg, 0.641 mmol), and TFA in MeCN (2.5 mL) was stirred at rt for 1 h. It was concentrated in vacuo and prep HPLC provided the title compound (30 mg, 0.104 mmol, 49% yield) as a pale yellow solid; $^1$H NMR (CDCl$_3$) δδ 8.40 (d, J=8.8 Hz, 1 H), 8.07 (d, J=8.6 Hz, 1 H), 7.90 (dd, J=8.6, 6.9 Hz, 1 H), 7.56 (dd, J=8.6, 6.9 Hz, 1 H), 5.26 (br. s, 1 H), 4.75 (d, J=5.7 Hz, 2 H), 3.10 (s, 3 H), 1.44 (s, 9 H); MS(ESI$^+$) m/z 289.2 (M+H)$^+$.

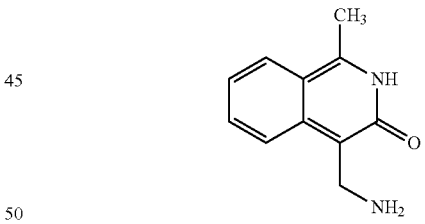

D) 4-(Aminomethyl)-1-methylisoquinoline-3(2H)-one

A mixture of t-Boc compound obtained above (30 mg, 0.104 mmo) and TFA (0.6 mL) in CH$_2$Cl$_2$ (5 mL) was stirred at rt for 70 min. It was concentrated in vacuo to obtain the title compound as a TFA salt of white solid (30 mg, 0.099 mmol, 99%). $^1$H NMR (MeOD-d$_4$) δ 8.00 (d, J=8.6 Hz, 1 H), 7.80 (d, J=9.0 Hz, 1 H), 7.68 (dd, J=8.6, 6.9 Hz, 1 H), 7.28 (dd, J=8.6, 6.9 Hz, 1 H), 4.45 (s, 2 H), 2.87 (s, 3 H), MS(ESI$^+$) m/z 172.2 (M−NH3)$^+$.

E) 5-(Ethyhtetrahydro-2H-pyran-4-yl)amino)-4-methyl-N-((1-methyl-3-oxo-2,3-dihydroisoquinolin-4-yl)methyl)-4'-(morpholinomethyl)-[1,1'-biphenyl]-3-carboxamide To a solution of 5-(ethyl(tetrahydro-2H-pyran-4-yl)amino)-4-methyl-4'-(morpholinomethyl)-[1,1'-biphenyl]-3-carboxylic acid (14.51 mg, 0.033 mmol) in DMF (2 mL) at rt was added HATU (13.84 mg, 0.036 mmol) solid. After 5 min this mixture was added to a solution of 4-(aminomethyl)-1-methylisoquinolin-3(2H)-one, TFA (10 mg, 0.033 mmol) and Hunig's Base (17.34 µL, 0.099 mmol) and it was stirred at rt for 1 h. The reaction mixture was directly purified by prep HPLC to obtain the title compound as 2 TFA salt of white solid (11 mg, 0.012 mmol, 38%) after lyophylizaion $^1$H NMR (MeOD-d$_4$) δ 8.17 (d, J=8.8 Hz, 1 H), 8.21 (d, J=8.1 Hz, 1 H), 7.92-7.82 (m, 2 H), 7.82 (d, J=8.1 Hz, 2 H), 7.71 (s, 1 H), 7.65 (d, J=8.1 Hz, 2 H), 7.49 (dd, J=7.8, 6.9 Hz, 1 H), 5.00 (s, 2 H), 4.43 (s, 2 H), 4.13-3.88 (m, 5 H), 3.78 (br. S. 2 H), 3.73-3.56 (m, 1 H), 3.50-3.35 (m, 4 H), 3.31-3.16 (m, 1 H), 3.01 (s, 3 H), 2.86 (s, 2 H), 2.43 (s, 3 H), 1.87-1.69 (m, 4 H), 1.02 (t, J=7.0 Hz, 3 H); MS(ESI$^+$) m/z 609.5 (M+H)$^+$.

Example 2

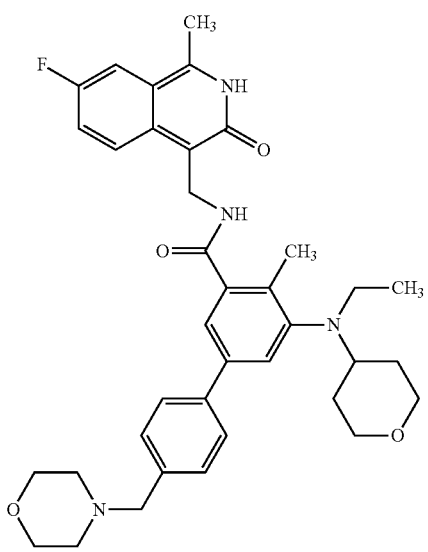 [SMILES: CCN(c1cc(-c2ccc(CN3CCOCC3)cc2)cc(C(=O)NCc2c(=O)[nH]c(C)c3cc(F)ccc23)c1C)C1CCOCC1]

5-(Ethyl(tetrahydro-2H-pyran-4-yl)amino)-N-((7-fluoro-1-methyl-3-oxo-2,3-dihydroisoquinolin-4-yl)methyl)-4-methyl-4'-(morpholinomethyl)-[1,1'-biphenyl]-3-carboxamide $^1$H NMR (MeOD-d$_4$) δ 8.14 (dd, J=9.6, 5.3 Hz, 1 H), 7.47-7.67 (m, 3 H), 7.62 (d, J=8.1 Hz, 2 H), 7.51 (d, J=8.1 Hz, 2 H), 7.33 (s, 1 H), 4.94 (s, 2 H), 3.80-3.94 (m, 8 H), 2.85-3.39 (m, 9 H), 2.82 (s, 3 H), 2.32 (s, 3 H), 1.60-1.74 (m, 4 H), 0.90 (t, J=7.0 Hz, 3H); MS(ESI$^+$) m/z 627.6 (M+H)$^+$.

Example 3

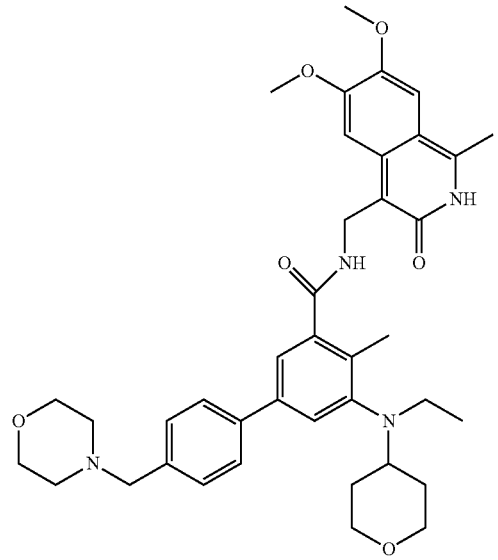 [SMILES: CCN(c1cc(-c2ccc(CN3CCOCC3)cc2)cc(C(=O)NCc2c(=O)[nH]c(C)c3cc(OC)c(OC)cc23)c1C)C1CCOCC1]

N-((6,7-Dimethoxy-1-methyl-3-oxo-2,3-dihydroisoquinolin-4-yl)methyl)-5-(ethyhtetrahydro-2H-pyran-4-yl)amino)-4-methyl-4'-(morpholinomethyl)-[1,1'-biphenyl]-3-carboxamide

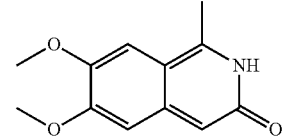 [SMILES: COc1cc2cc(=O)[nH]c(C)c2cc1OC]

A) 6,7-Dimethoxy-1-methylisoquinolin-3(2H)-one

To a solution of ethyl 2-(3,4-dimethoxyphenyl)acetate (4.0 g, 17.84 mmol) in acetic anhydride (8.41 ml, 89 mmol) at ice bath temperature under nitrogen was added perchloric acid (70% solution) (3.07 ml, 35.7 mmol) slowly. Yellow solid crashed out during addition of perchloric acid. The reaction mixture was stirred at 0° C. for 1 h. To the reaction mixture was added Et$_2$O and the solid was filtered off to give yellow solid. It was majorly the desired intermediate. The intermediate was transferred to a flask and to the solid was added water (8 mL) and ammonia hydroxide (14.88 ml, 107 mmol). The reaction mixture was stirred at rt for 1 h. The reaction mixture was filtered to give yellow solid, vacuum dried over night as the title compound (2.4 g, 61.4%). $^1$H NMR (DMSO-d$_6$) δ 7.13 (s, 1 H), 6.97 (s, 1 H), 6.51 (s, 1 H), 3.86 (d, J=2.0 Hz, 6 H), 2.68 (s, 3 H); MS(ESI$^+$) m/z 219.9 (M+H)$^+$.

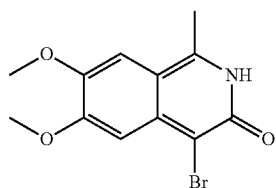 [SMILES: COc1cc2c(C)[nH]c(=O)c(Br)c2cc1OC]

B) 4-Bromo-6,7-dimethoxy-1-methylisoquinolin-3(2H)-one

The suspension of 6,7-dimethoxy-1-methylisoquinolin-3(2H)-one (1.0 g, 4.56 mmol) in CH$_3$CN (8 mL) was cooled with ice bath. To the mixture was added K$_2$CO$_3$ solution (0.79 g, 5.70 mmol) in water (10 mL) and cyanic bromide (0.53 g, 5.02 mmol) at 0° C. The reaction mixture was stirred at rt for 1 h. To the reaction mixture were added more CH$_3$CN (8 mL) and K$_2$CO$_3$ solution (1.0 M) (5 mL), and cyanic bromide (0.15 g) at rt. The reaction mixture was stirred at rt for another 2 h. The reaction mixture was filtered and the solid was collected, washed with water to give yellow solid as the title compound, and dried on high vacuum over night (0.8 g, 59%). $^1$H NMR (DMSO-d$_6$) δ 7.14 (s, 1 H), 7.01 (s, 1 H), 3.92 (s, 3 H), 3.88 (s, 3 H), 2.66 (s, 3 H); MS(ESI$^+$) m/z 299.8 (M+H)$^+$.

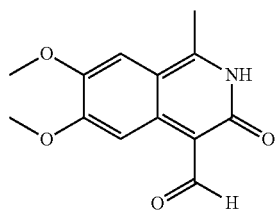 [SMILES: COc1cc2c(C)[nH]c(=O)c(C=O)c2cc1OC]

C) 6,7-Dimethoxy-1-methyl-3-oxo-2,3-dihydroisoquinoline-4-carbaldehyde

To a heterogenous solution of 4-bromo-6,7-dimethoxy-1-methylisoquinolin-3(2H)-one (0.8 g, 2.68 mmol) in diethyl ether (17 mL) was added MeLi (3.0 M solution in diethoxymethane) (1.34 mL, 4.03 mmol) slowly at −78° C. The resulting mixture was stirred for 15 min at −78° C. Here was added sec-BuLi (1.4 M solution in hexane) (2.49 mL, 3.49 mmol) slowly. After 30 min, more sec-BuLi— (1.4 M solution in hexane) (2.4 mL, 3.4 mmol) at −78° C. and the resulting mixture was stirred at −78° C. for another 1.5 h. DMF (1.247 mL, 16.10 mmol) was added slowly and the reaction mixture was stirred at −78° C. for 30 min, then warmed to rt and stirred for 30 min. The reaction mixture was quenched with 15 mL of 1N HCl solution. The mixture was filtered and washed with water to give yellow solid. The filtrate was extracted with CHCl$_3$:2-propanol (3:1) and dried over MgSO$_4$. The filtrate was concentrated in vacuo to give yellow solid and combined with the above solid as a mixture (0.18 g, 24%). It was used in the next step reaction without further purification. A small portion was purified by preparative HPLC and obtained small amount pure sample due to poor solubility in DMF, MeOH and CH$_3$CN. $^1$H NMR (DMSO-d$_6$) δ 10.33 (s, 1 H), 8.65 (s, 1 H), 7.16 (s, 1 H), 3.91 (s, 3 H), 3.85 (s, 3 H), 2.76 (s, 3 H); MS(ESI$^+$) m/z 247.8 (M+H)$^+$.

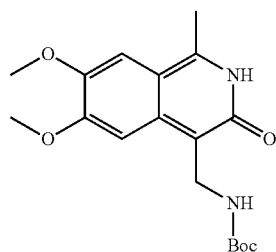 [SMILES: COc1cc2c(C)[nH]c(=O)c(CNC(=O)OC(C)(C)C)c2cc1OC]

D) tert-Butyl ((6,7-dimethoxy-1-methyl-3-oxo-2,3-dihydroisoquinolin-4-yl)methyl)carbamate To a suspension of the crude 6,7-dimethoxy-1-methyl-3-oxo-2,3-dihydroisoquinoline-4-carbaldehyde (170 mg, 0.7 mmol) (about 45% pure), tert-butyl carbamate (497 mg, 4.25 mmol), triethylsilane (494 mg, 4.25 mmol) in CH$_3$CN (12 mL) was added TFA (0.33 mL, 4.25 mmol). The resulting mixture was stirred at rt for 16 h. The reaction mixture was filtered to remove impurity. The filtrate was concentrated in vacuo and the residue was diluted with saturated NaHCO$_3$ solution and ethyl acetate. The organic layer was separated and washed with brine, concentrated in vacuo. The residue was dissolved in MeOH and filtered through syringe filter, purified by preparative HPLC. Fractions containing the product were combined, concentrated to give yellow solid as the title compound (40 mg, 20%). MS(ESI$^+$) m/z 349.0 (M+H)$^+$.

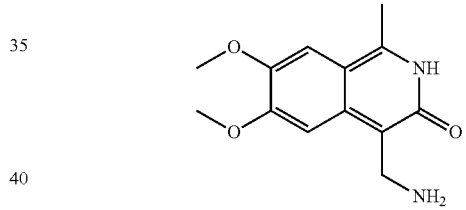

E) 4-(Aminomethyl)-6,7-dimethoxy-1-methylisoquinolin-3(2H)-one

To a suspension of tert-butyl ((6,7-dimethoxy-1-methyl-3-oxo-2,3-dihydroisoquinolin-4-yl)methyl)carbamate (30 mg, 0.086 mmol) in DCE (2 mL) was added HCl (4.0 M solution in dioxane) (0.13 mL, 0.52 mmol). The reaction mixture was stirred at rt for 1 h. The reaction mixture was concentrated in vacuo to give the title compound. The crude product was used in the next step coupling reaction. MS(ESI$^+$) m/z 231.8 (M−16)$^+$.

F) N-((6,7-Dimethoxy-1-methyl-3-oxo-2,3-dihydroisoquinolin-4-yl)methyl)-5-(ethyl(tetrahydro-2H-pyran-4-yl)amino)-4-methyl-4'-(morpholinomethyl)-[1,1'-biphenyl]-3-carboxamide To a solution of 5-(ethyl(tetrahydro-2H-pyran-4-yl)amino)-4-methyl-4'-(morpholinomethyl)-[1,1'-biphenyl]-3-carboxylic acid (16 mg, 0.036 mmol) in DMF (1 mL) was added HATU (20 mg, 0.051 mmol). The reaction mixture was stirred at rt for 3 min, followed by addition of a solution of 4-(aminomethyl)-6,7-dimethoxy-1-methylisoquinolin-3(2H)-one HCl salt (13 mg, 0.044 mmol) in DMF (1 mL) and NMM (0.04 mL, 0.37 mmol). The reaction mixture was stirred at rt for 45 min. The reaction mixture was diluted with ethyl acetate and brine. The organic layer was separated and concentrated in vacuo. The residue was purified by preparative HPLC. Fractions containing the product were combined, concentrated, and lyophilized to give light yellow solid as the title compound 2 TFA salt (10 mg, 30%). $^1$H NMR (MeOD-d$_4$) δ 7.73 (d, J=8.1 Hz, 2 H), 7.59 (d, J=8.1 Hz, 3 H), 7.50 (s, 1 H), 7.43 (br. s., 1 H), 7.23 (s, 1 H), 4.93 (s, 2 H), 4.40 (s, 2 H), 4.07 (s, 4 H), 3.97 (s, 3 H), 3.93-3.86 (m, 3 H), 3.75 (m, 2 H), 3.41-3.33 (m, 6 H), 3.28-3.07 (m, 3 H), 2.85 (s, 3 H), 2.31 (s, 3 H), 1.84-1.58 (m, 4 H), 0.91 (t, J=7.0 Hz, 3 H); MS(ESI$^+$) m/z 669.3 (M+H)$^+$.

Example 4

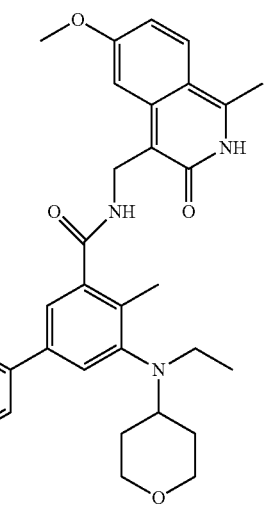

5-(Ethyhtetrahydro-2H-pyran-4-yl)amino)-N-((6-methoxy-1-methyl-3-oxo-2,3-dihydroisoquinolin-4-yl)methyl)-4-methyl-4'-(morpholinomethyl)-[1,1'-biphenyl]-3-carboxamide

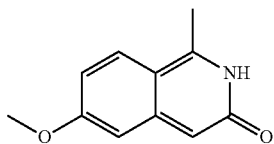

A) 6-Methoxy-1-methylisoquinolin-3(2H)-one

To a solution of methyl 2-(3-methoxyphenyl)acetate (3.5 g, 19.42 mmol) in acetic anhydride (9.16 ml, 97 mmol) at ice bath temperature under nitrogen was added perchloric acid (3.34 ml, 38.8 mmol) slowly. Yellow solid crashed out during addition of perchloric acid. The reaction mixture was stirred at 0° C. for 1.6 h. To the reaction mixture was added Et$_2$O and the solid was filtered to give light yellow solid. The intermediate was transferred to a flask and to the solid was added water (5 mL) and ammonium hydroxide (21.6 ml, 155 mmol). The reaction mixture was stirred at rt for over night. The reaction mixture was filtered to give yellow solid as the title compound (1.05 g, 28%). $^1$H NMR (DMSO-d$_6$) δ 7.84 (d, J=9.2 Hz, 1 H), 6.92 (d, J=2.4 Hz, 1 H), 6.82 (dd, J=9.2, 2.4 Hz, 1 H), 6.49 (s, 1 H), 3.84 (s, 3 H), 2.68 (s, 3 H); MS(ESI$^+$) m/z 189.8 (M+H)$^+$.

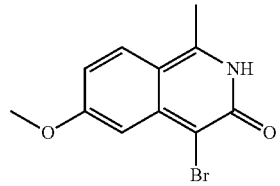

B) 4-Bromo-6-methoxy-1-methylisoquinolin-3(2H)-one

To the suspension of 6-methoxy-1-methylisoquinolin-3(2H)-one (1.0 g, 5.29 mmol) in acetonitrile (15 mL) was added K$_2$CO$_3$ (1.46 g, 10.57 mmol) in water (15 mL) solution and cyanic bromide (0.840 g, 7.93 mmol) at rt. The reaction mixture was stirred at rt for 2 h. The reaction mixture was filtered to give yellow solid. It was washed with water and dried in vacuo over night as the title compound (0.87 g. 61%). $^1$H NMR (DMSO-d$_6$) δ 7.88 (d, J=9.2 Hz, 1 H), 6.97 (br. s., 1 H), 6.84 (d, J=8.6 Hz, 1 H), 3.91 (s, 3 H), 2.69 (s, 3 H); MS(ESI$^+$) m/z 269.7 (M+H)$^+$.

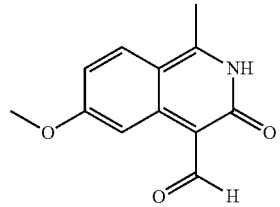 [SMILES: COc1ccc2c(C)[nH]c(=O)c(C=O)c2c1]

C) 6-methoxy-1-methyl-3-oxo-2,3-dihydroisoquinoline-4-carbaldehyde

To a solution of 4-bromo-6-methoxy-1-methylisoquinolin-3(2H)-one (0.35 g, 1.305 mmol) in diethyl ether (22 mL) at –78° C. was added NaH (60% suspension) (0.084 g, 2.09 mmol). The reaction mixture was stirred at rt for 30 min, followed by addition of sec-BuLi (1.4 M solution in hexane) (2.05 mL, 2.87 mmol) dropwise at –78° C. The reaction mixture was stirred at –78° C. for 2 h. To the reaction mixture was added DMF (0.81 mL, 10.44 mmol) slowly and the reaction mixture was stirred at –78° C. for 1 h, then warmed up to rt. To the reaction mixture was added HCl (13.1 mL, 13.05 mmol) to quench the reaction. The solid was filtered to give a yellow solid. The filtrate was extracted with CHCl$_3$:2-propanol (2.5:1). The organic layer was separated and concentrated in vacuo, lyophilized to give green solid of the crude product (0.1 g, 35%). It was combined with the filtered solid and used in the next step reaction without further purification. A small portion was purified by preparative HPLC for analytical purpose. $^1$H NMR (DMSO-d$_6$) δ 10.32 (s, 1 H), 8.62 (d, J=2.4 Hz, 1H), 7.93 (d, J=9.2 Hz, 1 H), 6.83 (d, J=9.2 Hz, 1 H), 6.51 (s, 1 H), 3.89 (s, 3 H), 2.77 (s, 3 H); MS(ESI$^+$) m/z 218.3 (M+H)$^+$.

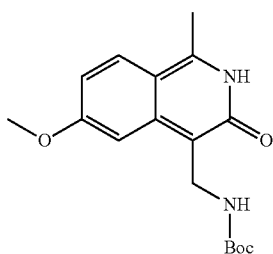 [SMILES: COc1ccc2c(C)[nH]c(=O)c(CNC(=O)OC(C)(C)C)c2c1]

D) tert-Butyl ((6-methoxy-1-methyl-3-oxo-2,3-dihydroisoquinolin-4-yl)methyl)carbamate To a suspension of 6-methoxy-1-methyl-3-oxo-2,3-dihydroisoquinoline-4-carbaldehyde (45 mg, 0.21 mmol) in acetonitrile (4 mL) (sonicated) were added tert-butyl carbamate (97 mg, 0.83 mmol), triethylsilane (96 mg, 0.83 mmol) and TFA (0.05 mL, 0.63 mmol). The resulting mixture was stirred at rt for 6 h. To the reaction mixture was added MeOH and the resulting mixture was concentrated in vacuo. The residue was dissolved in MeOH and filtered through syringe filter, purified by preparative HPLC. Fractions containing the product were combined, and lyophilized to give yellow solid as the title compound (25 mg, 38%). $^1$H NMR (CDCl$_3$) δ 7.91 (d, J=9.5 Hz, 1 H), 7.67 (s, 1 H), 7.13 (dd, J=9.4, 2.3 Hz, 1 H), 5.05 (br. s., 1 H), 4.72 (d, J=6.4 Hz, 2 H), 4.06 (s, 3H), 2.98 (s, 3 H), 1.44 (s, 9 H; MS(ESI$^+$) m/z 319.2 (M+H)$^+$.

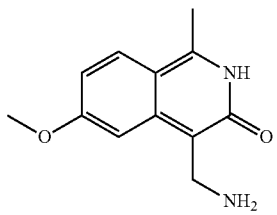 [SMILES: COc1ccc2c(C)[nH]c(=O)c(CN)c2c1]

E) 4-(Aminomethyl)-6-methoxy-1-methylisoquinolin-3(2H)-one

To a solution of tert-butyl ((6-methoxy-1-methyl-3-oxo-2,3-dihydroisoquinolin-4-yl)methyl)carbamate (25 mg, 0.079 mmol) in DCM (2 mL) was added HCl (4.0 M solution in dioxane) (0.4 mL, 1.6 mmol) slowly. The reaction mixture was stirred at rt for 2 h and was concentrated in vacuo to give light yellow solid as the title compound HCl salt (15 mg, 78%). MS(ESI$^+$) m/z 202.2 (M−16)$^+$.

F) 5-(Ethyl(tetrahydro-2H-pyran-4-yl)amino)-N-((6-methoxy-1-methyl-3-oxo-2,3-dihydroisoquinolin-4-yl)methyl)-4-methyl-4'-(morpholinomethyl)-[1,1'-biphenyl]-3-carboxamide To a solution of 5-(ethyl(tetrahydro-2H-pyran-4-yl)amino)-4-methyl-4'-(morpholinomethyl)-[1,1'-biphenyl]-3-carboxylic acid (25 mg, 0.057 mmol) in DMF (2 mL) was added HATU (31 mg, 0.08 mmol). The reaction mixture was stirred at rt for 5 min, followed by addition of a solution of 4-(aminomethyl)-6-methoxy-1-methylisoquinolin-3(2H)-one, HCl (15 mg, 0.06 mmol) in DMF (1 mL) and NMM (0.05 mL, 0.4 mmol). The reaction mixture was stirred at rt for 60 min. The reaction mixture was extracted with ethyl acetate. The organic layer was concentrated in vacuo and the residue was purified by preparative HPLC. Fractions containing the product were concentrated and lyophilized to give light yellow solid as the title compound 2 TFA salt (3 mg, 6%). $^1$H NMR (MeOD-d$_4$) δ 7.97 (d, J=9.5 Hz, 1 H), 7.74 (d, J=8.1 Hz, 2 H), 7.59 (d, J=8.1 Hz, 3 H), 7.50-7.36 (m, 2 H), 6.96 (dd, J=9.5, 2.2 Hz, 1 H), 4.92 (s, 2 H), 4.40 (s, 2 H), 4.14-3.63 (m, 12 H), 3.45-3.34 (m, 6 H), 2.84 (s, 3 H), 2.33 (s, 3 H), 1.86-1.56 (m, 4 H), 0.92 (t, J=6.9 Hz, 3 H); MS(ESI$^+$) m/z 639.8 (M+H)$^+$.

Example 6

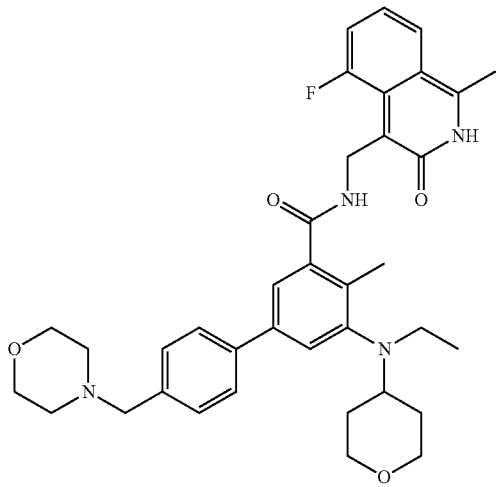 [SMILES: CCN(c1cc(-c2ccc(CN3CCOCC3)cc2)cc(C(=O)NCc2c(=O)[nH]c(C)c3cccc(F)c23)c1C)C1CCOCC1]

5-(Ethyl(tetrahydro-2H-pyran-4-yl)amino)-N-((5-fluoro-1-methyl-3-oxo-1,2,3,4-tetrahydroisoquinolin-4-yl)methyl)-4-methyl-4'-(morpholinomethyl)-[1,1'-biphenyl]-3-carboxamide

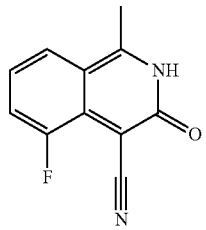

A) 5-Fluoro-1-methyl-3-oxo-2,3-dihydroisoquinoline-4-carbonitrile

To a suspension of 1-(2,3-difluorophenyl)ethanone (1.5 g, 9.61 mmol) and 2-cyanoacetamide (1.45 g, 17.3 mmol) in toluene (12 mL) was added NaH (0.85 g, 21.14 mmol) at rt. The reaction mixture was stirred at rt over the weekend. No desired product was detected. To the reaction mixture was added additional 0.6 g of 2-cyanoacetamide (1.45 g, 17.3 mmol) and 0.4 g of NaH and DMSO (16 mL). The reaction mixture was heated at 100° C. for 3 h. The reaction mixture was cooled down and to the mixture were added MeOH and 1 N HCl solution at ice bath temperature. Yellow solid crashed out and it was filtered to give yellow solid, washed with 1 N HCl, dried on vacuum as the desired product (0.43 g, 22.5%). $^1$H NMR (DMSO-d$_6$) δ 7.93 (d, J=8.1 Hz, 1 H), 7.56 (dd, J=12.3, 7.7 Hz, 1 H), 7.26 (br. s., 1 H), 2.87 (s, 3 H); MS(ESI$^+$) m/z 203.1 (M+H)$^+$.

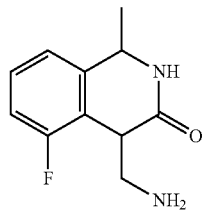

B) 4-(Aminomethyl)-5-fluoro-1-methyl-1,2-dihydroisoquinolin-3(4H)-one

To a suspension of 5-fluoro-1-methyl-3-oxo-2,3-dihydroisoquinoline-4-carbonitrile (0.12 g, 0.59 mmol) in acetic acid (3.4 ml, 59.4 mmol) were added NaOAc (97 mg, 1.19 mmol), PtO$_2$ (0.020 g, 0.089 mmol) and Pd—C(10% wt.) (0.095 g, 0.089 mmol). The mixture was hydrogenated in parr shaker at 45 psi for 3 h. The reaction mixture was filtered through celite and the filtrate was concentrated in vacuo to small amount. The residue was purified by preparative HPLC. Fractions containing the product were combined, concentrated and lyophilized to give white solid as the title compound TFA salt (60 mg, 31%). $^1$H NMR (MeOD-d$_4$) δ 8.68-8.43 (m, 1 H), 8.05 (br. s., 2 H), 7.51-7.31 (m, 1 H), 7.27-7.13 (m, 2 H), 4.89-4.62 (m, 1 H), 3.87 (ddd, J=15.7, 10.2, 5.2 Hz, 1 H), 3.30-3.01 (m, 2 H), 1.53-1.42 (m, 3 H); MS(ESI$^+$) m/z 209.2 (M+H)$^+$.

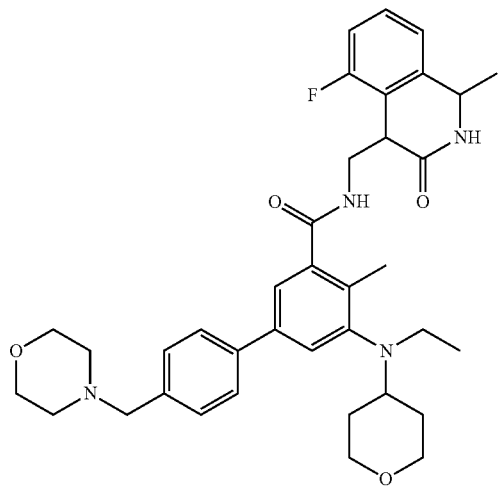 [SMILES: CCN(c1cc(-c2ccc(CN3CCOCC3)cc2)cc(C(=O)NCC2C(=O)NC(C)c3cccc(F)c32)c1C)C1CCOCC1]

C) 5-(Ethyhtetrahydro-2H-pyran-4-yl)amino)-N-((5-fluoro-1-methyl-3-oxo-1,2,3,4-tetrahydroisoquinolin-4-yl)methyl)-4-methyl-4'-(morpholinomethyl)-[1,1'-biphenyl]-3-carboxamide, Example 5

To a solution of 5-(ethyl(tetrahydro-2H-pyran-4-yl)amino)-4-methyl-4'-(morpholinomethyl)-[1,1'-biphenyl]-3-carboxylic acid (25 mg, 0.057 mmol) in DMF (1 mL) was added HATU (26 mg, 0.068 mmol). The reaction mixture was stirred at rt for 3 min, followed by the addition of a solution of 4-(aminomethyl)-5-fluoro-1-methyl-1,2-dihydroisoquinolin-3(4H)-one TFA (26 mg, 0.080 mmol) in DMSO (1 mL) and NMM (0.02 mL, 0.17 mmol). The reaction mixture was stirred at rt for 45 min. The reaction mixture was diluted with ethyl acetate and brine. The organic layer was separated and concentrated in vacuo. The residue was purified by preparative HPLC. Fractions containing the product were combined, concentrated, and lyophilized to give light yellow solid of Example 5 compound as a 2 TFA salt (38 mg, 78%). $^1$H NMR (MeOD-d$_4$) δ 7.92-7.79 (m, 2 H), 7.78-7.49 (m, 4 H), 7.44-6.95 (m, 4 H), 4.97-4.87 (m, 1 H), 4.74 (q, J=6.8 Hz, 1 H), 4.44 (s, 2 H), 4.16-3.67 (m, 10 H), 3.57-3.34 (m, 5 H), 3.01-2.81 (m, 1 H), 2.34 (s, 3 H), 1.90-1.69 (m, 4 H), 1.66-1.53 (m, 4 H), 0.98 (d, J=4.0 Hz, 3 H); MS(ESI$^+$) m/z 629.7 (M+H)$^+$.

D) 5-(Ethyhtetrahydro-2H-pyran-4-yl)amino)-N-((5-fluoro-1-methyl-3-oxo-1,2,3,4-tetrahydroisoquinolin-4-yl)methyl)-4-methyl-4'-(morpholinomethyl)-[1,1'-biphenyl]-3-carboxamide To 5-(ethyl(tetrahydro-2H-pyran-4-yl)amino)-N-((5-fluoro-1-methyl-3-oxo-1,2,3,4-tetrahydroisoquinolin-4-yl)methyl)-4-methyl-4'-(morpholinomethyl)-[1,1'-biphenyl]-3-carboxamide, 2 TFA (100 mg, 0.12 mmol) in DMF (2 mL) was added NaH (60% suspension in mineral oil) (70.0 mg, 1.75 mmol) at rt. The resulting mixture was heated at 100° C. for 1 h. and then cooled down. To the reaction mixture was added MeOH to destroy excess NaH. The resulting mixture was concentrated in vacuo. The residue was dissolved in MeOH, filtered through a syringe filter and the filtrate was purified by preparative HPLC. Fractions containing the product were combined, concentrated, and lyophilized to give light yellow solid of Example 6 compound as a 2 TFA salt (17 mg, 17%). $^1$H NMR (MeOD-d$_4$) δ 7.86 (d, J=8.6 Hz, 1 H), 7.74 (d, J=8.1 Hz, 2 H), 7.58 (d, J=8.4 Hz, 3 H), 7.38-7.16 (m, 3 H), 5.01 (d, J=2.6 Hz, 2 H), 4.40 (s, 2 H), 4.13-3.66 (m, 7 H), 3.51-3.33 (m, 8 H), 2.86 (s, 3 H), 2.37 (s, 3 H), 1.83-1.56 (m, 4 H), 0.92 (t, J=5.9 Hz, 3 H); MS(ESI$^+$) m/z 627.3 (M+H)$^+$.

Example 8

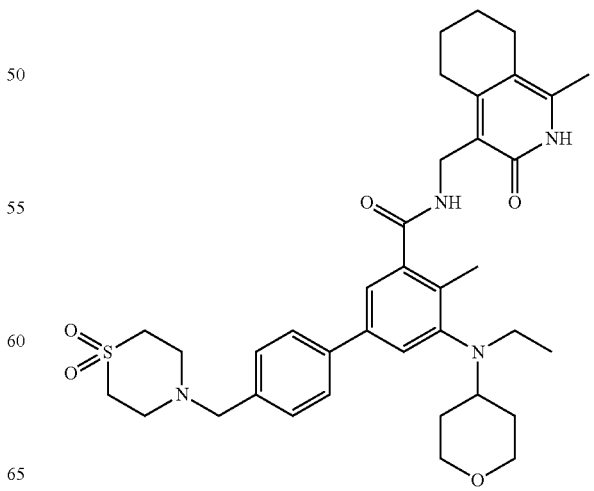

4'-((1,1-Dioxidothiomorpholino)methyl)-5-(ethyl(tetrahydro-2H-pyran-4-yl)amino)-4-methyl-N-((1-methyl-3-oxo-2,3,5,6,7,8-hexahydroisoquinolin-4-yl)methyl)-[1,1'-biphenyl]-3-carboxamide

A) 4-(4-(4,4,5,5-tetramethyl-1,3,2-Dioxaborolan-2-yl)benzyl)thiomorpholine 1,1-dioxide To a solution of 2-(4-(bromomethyl)phenyl)-4,4,5,5-tetramethyl-1,3,2-dioxaborolane (0.50 g, 1.68 mmol) in DMF (8 mL) were added $K_2CO_3$ (0.58 g, 4.21 mmol) and thiomorpholine 1,1-dioxide (0.27 g, 2.02 mmol). The reaction mixture was stirred at rt for 2 h. The reaction mixture was diluted with water and ethyl acetate. The organic layer was separated and washed with brine, dried over $MgSO_4$. The filtrate was concentrated in vacuo to give the title compound as a white solid (0.53 g, 89%). $^1$H NMR (DMSO-$d_6$) δ 7.65 (d, J=8.1 Hz, 2 H), 7.35 (d, J=7.9 Hz, 2 H), 3.68 (s, 2 H), 3.16-3.01 (m, 4 H), 2.85 (dd, J=6.2, 4.0 Hz, 4 H), 1.29 (s, 12 H); MS(ESI$^1$) m/z 352.1 (M+H)$^+$.

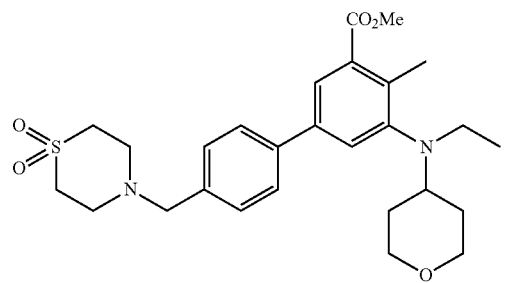 [SMILES: CCN(c1cc(-c2ccc(CN3CCS(=O)(=O)CC3)cc2)cc(C(=O)OC)c1C)C1CCOCC1]

B) Methyl 4'-((1,1-dioxidothiomorpholino)methyl)-5-(ethyhtetrahydro-2H-pyran-4-yl)amino)-4-methyl-[1,1'-biphenyl]-3-carboxylate To a solution of 4-(4-(4,4,5,5-tetramethyl-1,3,2-dioxaborolan-2-yl)benzyl)thiomorpholine 1,1-dioxide (0.26 g, 0.73 mmol) and methyl 5-bromo-3-(ethyl(tetrahydro-2H-pyran-4-yl)amino)-2-methylbenzoate (0.20 g, 0.56 mmol) (Ref WO 2012/142504) in 1,4-dioxane (8 mL) was added 2.0 M aqueous solution of $Na_2CO_3$ (0.84 mL, 1.684 mmol). The reaction mixture was purged with nitrogen stream for 3 min, followed by addition of $PdCl_2$(dppf) (0.062 g, 0.084 mmol). The resulting mixture was then heated at 100° C. for 2 h under nitrogen stream. The reaction mixture was cooled down, filtered through a celite pad and the pad was washed with ethyl acetate. The filtrate was concentrated in vacuo and the residue was purified by preparative HPLC. Fractions containing the product were combined, concentrated to small amount. The residue was basified with saturated $NaHCO_3$ solution and extracted with $CHCl_3$:2-propanol (3:1). The organic layer was separated and dried over $MgSO_4$. The filtrate was concentrated in vacuo. to give the title compound as a white solid (0.22 g, 78%). $^1$H NMR (MeOH-$d_4$) δ 7.79 (d, J=2.0 Hz, 1 H), 7.65-7.54 (m, 3 H), 7.46 (d, J=8.1 Hz, 2 H), 3.94 (brs., 2 H), 3.91 (s, 3 H), 3.74 (s, 2 H), 3.38 (td, J=11.7, 2.2 Hz, 2 H), 3.21-3.06 (m, 7 H), 3.00 (dd, J=6.7, 3.6 Hz, 4 H), 2.52 (s, 3 H), 1.86-1.72 (m, 2 H), 1.70-1.54 (m, 2 H), 0.91 (t, J=7.0 Hz, 3 H); MS(ESI$^+$) m/z 501.4 (M+H)$^+$.

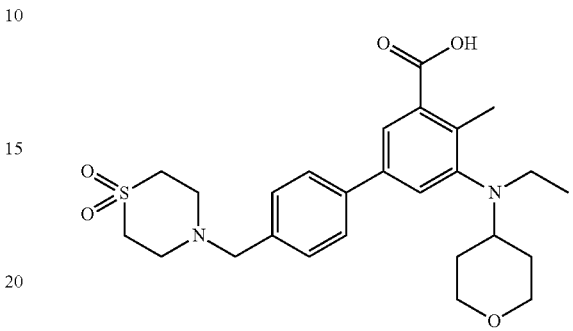

C) 4'-((1,1-Dioxidothiomorpholino)methyl)-5-(ethyl(tetrahydro-2H-pyran-4-yl)amino)-4-methyl-[1,1'-biphenyl]-3-carboxylic acid To a solution of methyl 4'-((1,1-dioxidothiomorpholino)methyl)-5-(ethyl(tetrahydro-2H-pyran-4-yl)amino)-4-methyl-[1,1'-biphenyl]-3-carboxylate (220 mg, 0.44 mmol) in THF (4 mL) and MeOH (2 mL) was added LiOH aqueous solution (3.5 mL, 7.10 mmol). The resulting mixture was stirred at rt for 8 h. To the reaction mixture was added 2 N HCl solution to adjust pH to 1. The resulting mixture was extracted with ethl acetate. The organic layer was separated, washed with brine and dried over $MgSO_4$. The filtrate was concentrated in vacuo. LC-MS showed no product of the organic layer. To the aqueous layer was added $NaHCO_3$ solid to adjust pH to 5-6. The resulting mixture was extracted with $CHCl_3$:2-propanol (2.5:1). The organic layer was separated and dried over $MgSO_4$. The filtrate was concentrated in vacuo to give the title compound as a white solid (205 mg, 92%). $^1$H NMR (DMSO-$d_6$) δ 7.71 (d, J=2.0 Hz, 1 H), 7.61 (d, J=8.1 Hz, 2 H), 7.56 (d, J=1.3 Hz, 1 H), 7.42 (d, J=8.1 Hz, 2 H), 3.91-3.78 (m, 2 H), 3.71 (s, 2 H), 3.35-3.21 (m, 2 H), 3.20-3.00 (m, 7 H), 2.89 (dd, J=6.2, 3.5 Hz, 4 H), 2.45 (s, 3 H), 1.67 (d, J=10.8 Hz, 2 H), 1.50 (dd, J=12.1, 4.0 Hz, 2 H), 0.83 (t, J=7.0 Hz, 3 H); MS(ESI$^+$) m/z 487.3 (M+H)$^+$.

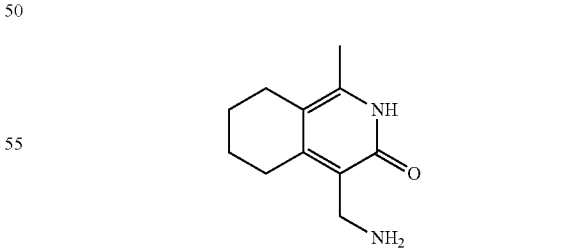

D) 4-(Aminomethyl)-1-methyl-5,6,7,8-tetrahydroisoquinolin-3(2H)-one

To a suspension of 1-methyl-3-oxo-2,3,5,6,7,8-hexahydroisoquinoline-4-carbonitrile (0.49 g, 2.60 mmol) (source: Princeton Bio Molecule) in acetic acid (15 mL) were added NaOAc (0.38 g, 4.69 mmol), Pd—C(0.42 g, 0.39 mmol) and Pt₂O (60 mg, 0.26 mmol). The mixture was hydrogenated on parr shaker at 45 psi for 6 h. The reaction mixture was filtered through celite and the filtrate was concentrated in vacuo to small amount. To the residue was added saturatedNaHCO₃ solution to adjust pH to 8. The resulting mixture was extracted with CHCl₃:2-propanol (2:1) three times. The organic layer was separated, combined and dried over MgSO₄. The filtrate was concentrated in vacuo to give the title compound as a light yellow solid, dried on vacuum pump (390 mg, 78%). ¹H NMR (MeOH-d₄) δ 3.73 (s, 2 H), 2.89-2.70 (m, 2 H), 2.51 (brs., 2 H), 2.22 (s, 3 H), 1.77 (dt, J=6.8, 3.3 Hz, 4 H); MS(ESI⁺) m/z 193.3 (M+H)⁺.

E) 4'-((1,1-Dioxidothiomorpholino)methyl)-5-(ethyl(tetrahydro-2H-pyran-4-yl)amino)-4-methyl-N-((1-methyl-3-oxo-2,3,5,6,7,8-hexahydroisoquinolin-4-yl)methyl)-[1,1'-biphenyl]-3-carboxamide To a solution of 4'-((1,1-dioxidothiomorpholino)methyl)-5-(ethyl(tetrahydro-2H-pyran-4-yl)amino)-4-methyl-[1,1'-biphenyl]-3-carboxylic acid (31 mg, 0.064 mmol) in DMF (1.5 mL) was added HATU (30 mg, 0.080 mmol) and 4-(aminomethyl)-1-methyl-5,6,7,8-tetrahydroisoquinolin-3(2H)-one (13.5 mg, 0.070 mmol) and NMM (0.03 mL, 0.26 mmol). The reaction mixture was stirred at rt for 2 h. The reaction mixture was concentrated in vacuo and the residue was purified by preparative HPLC. Fractions containing the product were combined, concentrated, and lyophilized to give the title compound 2 TFA salt as a white solid (48 mg, 81%). ¹H NMR (MeOH-d₄) δ 7.73 (d, J=8.1 Hz, 3 H), 7.55 (d, J=8.1 Hz, 3 H), 4.54 (s, 2 H), 4.06 (brs., 2 H), 3.99-3.96 (m, 3 H), 3.43-3.37 (m, 3 H), 3.30-3.28 (m., 5 H), 2.96 (m, 3 H), 2.54 (m, 3 H), 2.43 (s, 3 H), 2.26 (s, 4 H), 1.86-1.73 (m, 9 H), 1.02 (t, J=6.8 Hz, 3 H); MS(ESI⁺) m/z 661.7 (M+H)⁺.

Example 13

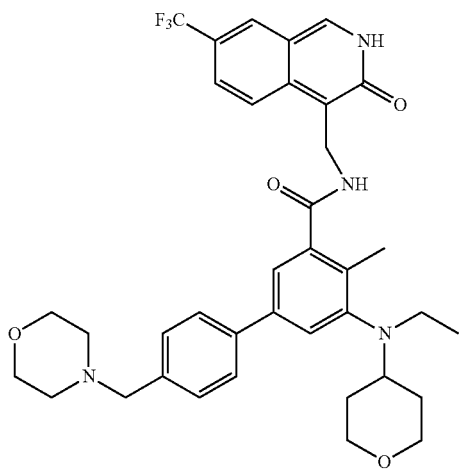 [SMILES: CCN(c1cc(-c2ccc(CN3CCOCC3)cc2)cc(C(=O)NCc2c(=O)[nH]cc3cc(C(F)(F)F)ccc23)c1C)C1CCOCC1]

5-(Ethyl(tetrahydro-2H-pyran-4-yl)amino)-4-methyl-4'-(morpholinomethyl)-N-((3-oxo-7-(trifluoromethyl)-2,3-dihydroisoquinolin-4-yl)methyl)-[1,1'-biphenyl]-3-carboxamide

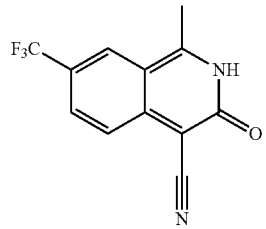 [SMILES: Cc1[nH]c(=O)c(C#N)c2ccc(C(F)(F)F)cc12]

A) 1-Methyl-3-oxo-7-(trifluoromethyl)-2,3-dihydroisoquinoline-4-carbonitrile

To a solution of 1-(2-fluoro-5-(trifluoromethyl)phenyl)ethanone (2.0 g, 9.70 mmol) in DMSO (15 mL) were added 2-cyanoacetamide (1.79 g, 21.35 mmol) and NaH (60% suspension in mineral oil) (0.89 g, 22.32 mmol) at rt. The reaction mixture was exothermic and stirred at rt for 10 min, then heated at 85° C. for 3 h. The reaction mixture was cooled down and to the reaction mixture was added ice, 1 N HCL solution to adjust pH to 3. Yellow solid crashed out. The solid was filtered, and washed with water, DCM to give the title compound as a yellow solid (0.86 g, 35%). ¹H NMR (DMSO-d₆) δ 8.36 (s, 1 H), 7.90 (d, J=8.8 Hz, 1 H), 7.70 (d, J=8.8 Hz, 1 H), 2.91 (s, 3 H); MS(ESI⁺) m/z 253.2 (M+H)⁺.

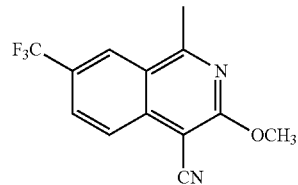 [SMILES: COc1nc(C)c2cc(C(F)(F)F)ccc2c1C#N]

B) 3-Methoxy-1-methyl-7-(trifluoromethyl)isoquinoline-4-carbonitrile

To a suspension of 1-methyl-3-oxo-7-(trifluoromethyl)-2,3-dihydroisoquinoline-4-carbonitrile (0.49 g, 1.94 mmol) in DCM (45 mL) (sonicated) was added Trimethyloxonium tetrafluoroborate (0.40 g, 2.72 mmol) and proton sponge (0.75 g, 3.50 mmol) at rt. The reaction mixture was stirred at rt over night. The reaction mixture was diluted with brine and DCM. The organic layer was separated and washed with 1 N HCl solution, dried over MgSO₄. The filtrate was concentrated in vacuo to give yellow solid. The residue was dissolved in DCM, filtered through a syringe filter and purified by flash chromatography (0 to 20% ethyl acetate in hexane) to give the title compound as a white solid (0.23 g, 45%). ¹H NMR (CDCl₃) δ 8.38 (s, 1 H), 8.14 (d, J=8.8 Hz, 1 H), 7.92 (dd, J=8.8, 1.5 Hz, 1 H), 4.21 (s, 3 H), 3.03 (s, 3 H); MS(ESI⁺) m/z 267.0 (M+H)⁺.

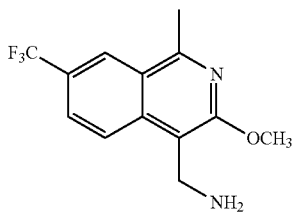 [SMILES: COc1nc(C)c2cc(C(F)(F)F)ccc2c1CN]

C) (3-Methoxy-1-methyl-7-(trifluoromethyl)isoquinolin-4-yl)methanamine

To a solution of 3-methoxy-1-methyl-7-(trifluoromethyl) isoquinoline-4-carbonitrile (0.23 g, 0.86 mmol) in MeOH (12 mL) and ethyl acetate (1 mL) were added acetic acid (1.0 mL, 17.47 mmol) and PtO$_2$ (30 mg, 0.13 mmol). The reaction mixture was evacuated and hydrogenated under hydrogen balloon at rt for 7.5 h. The reaction mixture was filtered through a celite pad and the filtrate was concentrated in vacuo. The residue was mixed with 0.4 mL of NMM amine and MeOH, filtered through a syringe filter, purified by preparative HPLC. Fractions containing the product were concentrated and lyophilized to give the title compound TFA salt as a white solid (166 mg, 50%). $^1$H NMR (MeOH-d$_4$) δ 8.52 (s, 1 H), 8.22 (d, J=9.0 Hz, 1 H), 7.93 (dd, J=9.0, 1.8 Hz, 1 H), 4.56 (s, 2 H), 4.18 (s, 3 H), 3.01 (s, 3 H); MS(ESI$^+$) m/z 271.2 (small) (M+H)$^+$ and 254.0 (M−16) (base).

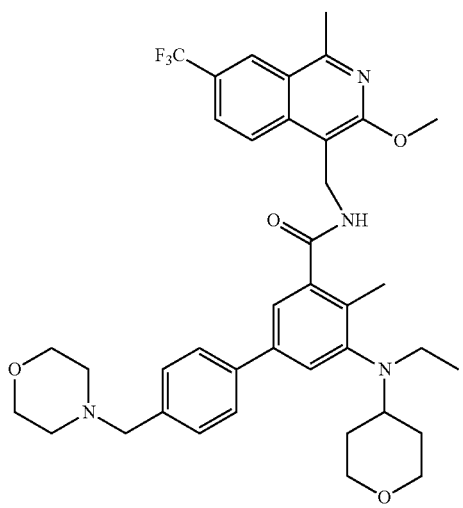 [SMILES: CCN(c1cc(-c2ccc(CN3CCOCC3)cc2)cc(C(=O)NCc2c(OC)nc(C)c3cc(C(F)(F)F)ccc23)c1C)C1CCOCC1]

D) 5-(Ethyl(tetrahydro-2H-pyran-4-yl)amino)-N-((3-methoxy-1-methyl-7-(trifluoromethyl)isoquinolin-4-yl)methyl)-4-methyl-4'-(morpholinomethyl)-[1,1'-biphenyl]-3-carboxamide To a solution of 5-(ethyl(tetrahydro-2H-pyran-4-yl) amino)-4-methyl-4'-(morpholinomethyl)-[1,1'-biphenyl]-3-carboxylic acid (36 mg, 0.082 mmol) in DMF (2 mL) were added HATU (38 mg, 0.10 mmol). The reaction mixture was stirred at rt for 5 min, followed by addition of (3-methoxy-1-methyl-7-(trifluoromethyl)isoquinolin-4-yl)methanamine TFA salt (38 mg, 0.10 mmol) NMM (0.06 mL, 0.49 mmol). The resulting mixture was stirred at rt for 1 h. The reaction mixture was diluted with ethyl acetate and brine. The organic layer was separated and concentrated in vacuo. The residue was purified by preparative HPLC. Fractions containing the product were concentrated and lyophilized to give the title compound 2TFA salt as a white solid (62 mg, 82%). $^1$H NMR (CDCl$_3$) δ 8.40 (d, J=9.0 Hz, 1 H), 8.34 (s, 1 H), 7.82 (dd, J=9.0, 1.8 Hz, 1 H), 7.58-7.52 (m, 2 H), 7.50-7.43 (m, 2 H), 7.41 (s, 1 H), 7.33 (s, 1 H), 6.33 (t, J=5.7 Hz, 1 H), 5.08 (d, J=5.7 Hz, 2 H), 4.22 (s, 2 H), 4.12 (s, 3 H), 4.05-3.85 (m, 6 H), 3.49 (d, J=11.7 Hz, 2 H), 3.38-3.20 (m, 6 H), 2.97 (s, 3 H), 2.91 (d, J=9.7 Hz, 1 H), 2.38 (s, 3 H), 1.76 (d, J=2.9 Hz, 4 H), 0.92 (t, J=6.9 Hz, 3 H); MS(ESI$^+$) m/z 691.5 (M+H)$^+$.

E) 5-(Ethyl(tetrahydro-2H-pyran-4-yl)amino)-4-methyl-4'-(morpholinomethyl)-N-((3-oxo-7-(trifluoromethyl)-2,3-dihydroisoquinolin-4-yl)methyl)-[1,1'-biphenyl]-3-carboxamide To 5-(ethyl(tetrahydro-2H-pyran-4-yl)amino)-N-((3-methoxy-1-methyl-7-(trifluoromethyl)isoquinolin-4-yl) methyl)-4-methyl-4'-(morpholinomethyl)-[1,1'-biphenyl]-3-carboxamide 2TFA salt (25 mg, 0.027 mmol) in the flask was added HBr (33% W/W solution in acetic acid) (1.5 mL, 8.56 mmol). The reaction mixture was heated at 75° C. for 1 h. The reaction mixture was cooled down and diluted with Na$_2$HPO$_4$ solution to adjust pH to 8. The resulting mixture was extracted with ethyl acetate. The organic layer was separated and concentrated in vacuo to give the title compound as a yellow solid (9 mg, 46%). $^1$H NMR (CDCl$_3$) δ 8.25 (d, J=9.2 Hz, 1 H), 8.03 (s, 1 H), 7.68 (dd, J=9.2, 1.8 Hz, 1 H), 7.42 (d, J=8.1 Hz, 2 H), 7.36-7.28 (m, 4 H), 6.87 (t, J=5.7 Hz, 1 H), 5.03 (d, J=5.7 Hz, 2 H), 3.94 (d, J=11.4 Hz, 2 H), 3.69 (t, J=4.5 Hz, 4 H), 3.46 (brs., 2 H), 3.31 (td, J=11.1, 3.2 Hz, 2 H), 3.10 (q, J=7.0 Hz, 2 H), 3.01 (qd, J=9.7, 4.6 Hz, 1 H), 2.82 (s, 3 H), 2.44 (brs., 4 H), 2.36 (s, 3 H), 1.70-1.65 (m, J=9.4, 4.1 Hz, 4 H), 0.89 (t, J=7.0 Hz, 3 H); MS(ESI$^+$) m/z 677.5 (M+H)$^+$.

Example 17

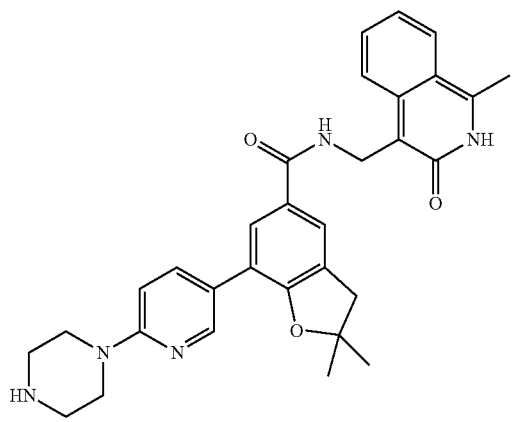 [SMILES: Cc1[nH]c(=O)c(CNC(=O)c2cc3c(c(-c4ccc(N5CCNCC5)nc4)c2)OC(C)(C)C3)c2ccccc12]

2,2-Dimethyl-N-((1-methyl-3-oxo-2,3-dihydroisoquinolin-4-yl)methyl)-7-(6-(piperazin-1-yl)pyridin-3-yl)-2,3-dihydrobenzofuran-5-carboxamide

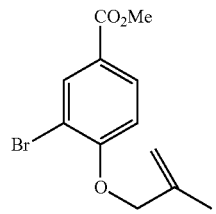 [SMILES: C=C(C)COc1ccc(C(=O)OC)cc1Br]

A) Methyl 3-bromo-4-((2-methylallyl)oxy)benzoate

Methyl 3-bromo-4-hydroxybenzoate (2.2 g, 9.52 mmol) was dissolved in acetonitrile (20 mL) under nitrogen. Potassium carbonate (1.579 g, 11.43 mmol) was added and stirring continued for 5 minutes. 3-Bromo-2-methylprop-1-ene (1.152 ml, 11.43 mmol) was then added and the reaction stirred overnight. The reaction was quenched with water and transferred to a separatory funnel. The reaction was extracted with ether. The organic layer was washed with water and then brine. The organic phase was dried over magnesium sulfate, filtered and evaporated. The crude material was applied to an 80 g Isco silica gel column and eluted with 0-25% ethyl acetate in hexanes. Evaporation of the appropriate fractions gave methyl 3-bromo-4-((2-methylallyl)oxy)benzoate (2.39 g, 8.21 mmol, 86% yield) as a colorless solid. $^1$H NMR (400 MHz, CHLOROFORM-d) δ 8.28 (d, J=2.0 Hz, 1H), 7.98 (dd, J=8.7, 2.1 Hz, 1H), 6.93 (d, J=8.6 Hz, 1H), 5.20 (t, J=1.1 Hz, 1H), 5.12-4.98 (m, 1H), 4.60 (s, 2H), 3.93 (s, 3H), 1.90 (d, J=0.4 Hz, 3H).

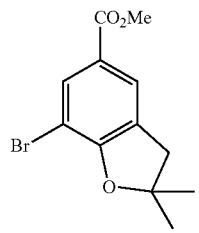

B) Methyl 7-bromo-2,2-dimethyl-2,3-dihydrobenzofuran-5-carboxylate

A reaction vial was charged with methyl 3-bromo-4-((2-methylallyl)oxy)benzoate (456 mg, 1.599 mmol) and Dowtherm (0.5 mL). The vial was sealed and heated to 200° C. for 2 hours. The reaction was cooled and applied directly to a 40 g Isco silica gel column and eluted with 0-20% ethyl acetate in hexanes. Evaporation of the appropriate fractions gave methyl 3-bromo-4-hydroxy-5-(2-methylallyl)benzoate (352 mg, 1.235 mmol, 77% yield) as a viscous oil. 1H-NMR suggested the presence of some minor impurities, but the material was carried into the next step. The material was dissolved in formic acid (6 mL) under nitrogen. The reaction was warmed to 110° C. for 3 hours. The reaction was then cooled and stirred for 5 days. The material was transferred to a reparatory funnel and diluted with ether. The organic layer was washed with saturated sodium bicarbonate solution until weakly alkaline and then brine. The ether layer was dried over magnesium sulfate, filtered and evaporated. The crude product was applied to a 40 g Isco silica gel column and eluted with 0-20% ethyl acetate in hexanes. Concentration of the appropriate fractions provided methyl 7-bromo-2,2-dimethyl-2,3-dihydrobenzofuran-5-carboxylate (206 mg, 0.708 mmol, 57.4% yield) as a colorless solid. $^1$H NMR (400 MHz, DMSO-d$_6$) δ 7.93-7.88 (m, 1H), 7.79 (q, J=1.2 Hz, 1H), 3.83 (s, 3H), 3.20 (s, 2H), 1.49 (s, 6H).

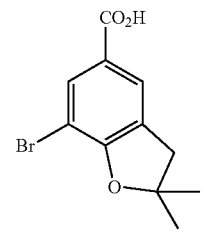

C) 7-Bromo-2,2-dimethyl-2,3-dihydrobenzofuran-5-carboxylic acid

Methyl 7-bromo-2,2-dimethyl-2,3-dihydrobenzofuran-5-carboxylate (192 mg, 0.673 mmol) was dissolved in tetrahydrofuran-water (3:1. 4 mL). Lithium hydroxide solution (1347 μl, 1.347 mmol, 1 N) was added. The reaction was warmed to 55° C. and stirred overnight. The reaction was cooled and neutralized with 1 N hydrochloric acid (1.35 mL). he reaction was concentrated under a stream of nitrogen to generate a colorless precipitate. The solid was filtered, rinsed well with water and then hexanes. Air drying then provided 7-bromo-2,2-dimethyl-2,3-dihydrobenzofuran-5-carboxylic acid (175 mg, 0.633 mmol, 94% yield) as a colorless solid. $^1$H NMR (400 MHz, DMSO-d$_6$) δ 12.80 (br. s., 1H), 7.87 (d, J=1.5 Hz, 1H), 7.76 (d, J=1.5 Hz, 1H), 3.19 (s, 2H), 1.49 (s, 6H).

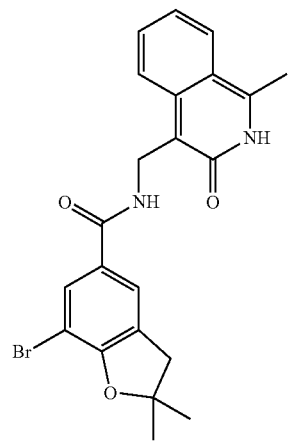 [SMILES: Cc1[nH]c(=O)c(CNC(=O)c2cc(Br)c3c(c2)CC(C)(C)O3)c2ccccc12]

D) 7-Bromo-2,2-dimethyl-N-((1-methyl-3-oxo-2,3-dihydroisoquinolin-4-yl)methyl)-2,3-dihydrobenzofuran-5-carboxamide To a solution of 4-(aminomethyl)-1-methylisoquinolin-3(2H)-one, HCl (13.48 mg, 0.06 mmol, hydrochloride salt of Intermediate 1D) in DMF (1.0 mL) was added 7-bromo-2,2-dimethyl-2,3-dihydrobenzofuran-5-carboxylic acid (16.27 mg, 0.060 mmol) and triethylamine (41.8 μl, 0.300 mmol). The reaction was initiated with the addition of BOP (31.8 mg, 0.072 mmol). After stirring overnight, LCMS analysis showed a significant peak for the desired product and a major non-polar peak that appeared to be bis-acylated. The crude product was purified by RP-HPLC (methanol-water gradient+0.1% TFA). Concentration of the product containing peak gave 7 mg of a yellow solid. The non-polar peak was concentrated and dissolved in ca. 2 mL of methanol-ammonia (7 N). LCMS analysis suggests that the by-product is cleanly converted to a 1:1 mixture of desired product and the carboxamide of the acid starting material. The reaction was evaporated and recombined with the previously isolated product. The combined materials were dissolved in DMF and purified by RP-HPLC (methanol-water gradient+0.1% TFA). The appropriate fractions were evaporated to give 7-bromo-2,2-dimethyl-N-((1-methyl-3-oxo-2,3-dihydroisoquinolin-4-yl)methyl)-2,3-dihydrobenzofuran-5-carboxamide, TFA (13.2 mg, 0.023 mmol, 37.6% yield) as a pale yellow solid. $^1$H NMR (400 MHz, CHLOROFORM-d) δ 8.52 (d, J=8.8 Hz, 1H), 8.07 (d, J=8.6 Hz, 1H), 7.95-7.87 (m, 1H), 7.74 (d, J=1.7 Hz, 1H), 7.60-7.53 (m, 1H), 7.49 (d, J=1.5 Hz, 1H), 6.83 (t, J=6.0 Hz, 1H), 5.06 (d, J=6.2 Hz, 2H), 3.12 (s, 2H), 1.54 (s, 6H); MS(ESI$^+$) m/z 441 (M+H)$^+$.

E) 2,2-Dimethyl-N-((1-methyl-3-oxo-2,3-dihydroisoquinolin-4-yl)methyl)-7-(6-(piperazin-1-yl)pyridin-3-yl)-2,3-dihydrobenzofuran-5-carboxamide A reaction vial was charged with 1-(5-(4,4,5,5-tetramethyl-1,3,2-dioxaborolan-2-yl)pyridin-2-yl)piperazine (11.46 mg, 0.040 mmol), 7-bromo-2,2-dimethyl-N-((1-methyl-3-oxo-2,3-dihydroisoquinolin-4-yl)methyl)-2,3-dihydrobenzofuran-5-carboxamide, TFA (11 mg, 0.020 mmol) and DMF (0.5 mL). A solution of sodium carbonate (87 μl, 0.087 mmol, 1 M) was added. Nitrogen was bubbled through the reaction for ca. 15 minutes. Tetrakis(triphenylphosphine)palladium(0) (2.289 mg, 1.981 μmol) was added and degassing was continued for a few minutes. The vial was then sealed and heated to 100° C. overnight. The cooled reaction was then diluted with DMF (1.5 mL) and filtered. The final compound was purified by reverse phase HPLC using the following conditions: Column—Waters XBridge C18, 19×250 mm, 5-nm particles. Solvent—acetonitrile-water gradient containing 10 mM ammonium acetate. Evaporation of the product containing fractions gave the product (4.7 mg, 45%). $^1$H NMR (500 MHz, DMSO-d$_6$) δ 8.56 (br. s., 1H), 8.60-8.54 (m, 1H), 8.47 (s, 1H), 8.00 (d, J=8.8 Hz, 1H), 7.89-7.83 (m, 2H), 7.80 (s, 1H), 7.66 (s, 1H), 7.55 (t, J=7.6 Hz, 1H), 7.25 (t, J=7.6 Hz, 1H), 6.86 (d, J=9.1 Hz, 1H), 4.77 (d, J=4.4 Hz, 2H), 3.47 (br. s., 4H), 3.05 (s, 2H), 2.82 (br. s., 4H), 2.79 (s, 3H), 1.43 (s, 6H); MS(ESI$^+$) m/z 524 (M+H)$^+$.

The following examples were prepared according to the procedure for the synthesis of Examples shown above.

| Ex. No. | Structure | Name | LCMS (M + H) |
|---|---|---|---|
| 1 | 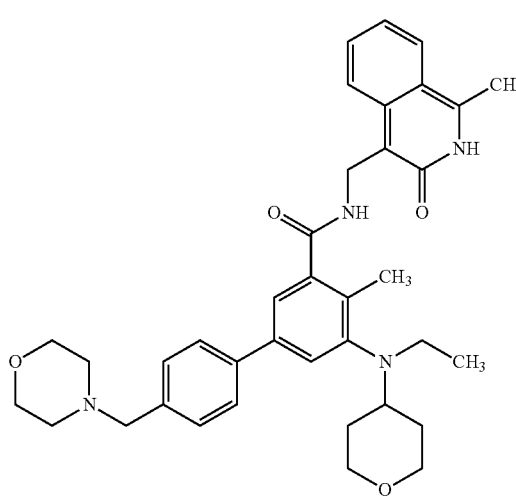 | 5-(Ethyl(tetrahydro-2H-pyran-4-yl)amino)-4-methyl-N-((1-methyl-3-oxo-2,3-dihydroisoquinolin-4-yl)methyl)-4'-(morpholinomethyl)-[1,1'-biphenyl]-3-carboxamide | 609.5 |

| Ex. No. | Structure | Name | LCMS (M + H) |
|---|---|---|---|
| 2 | 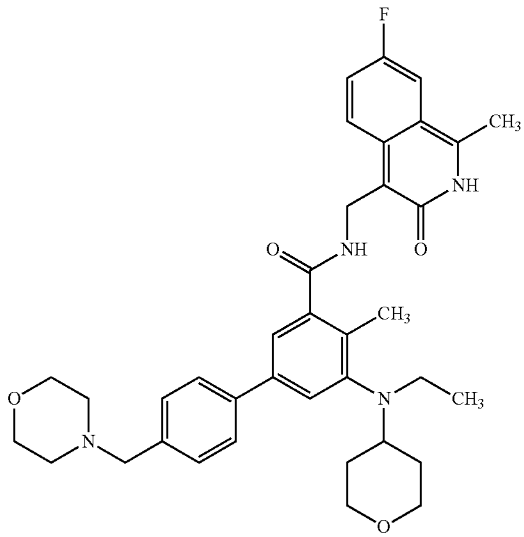 [SMILES: CCN(c1cc(-c2ccc(CN3CCOCC3)cc2)cc(C(=O)NCc2c(=O)[nH]c(C)c3cc(F)ccc23)c1C)C1CCOCC1] | 5-(Ethyl(tetrahydro-2H-pyran-4-yl)amino)-N-((7-fluoro-1-methyl-3-oxo-2,3-dihydroisoquinolin-4-yl)methyl)-4-methyl-4'-(morpholinomethyl)-[1,1'-biphenyl]-3-carboxamide | 627.6 |
| 3 | 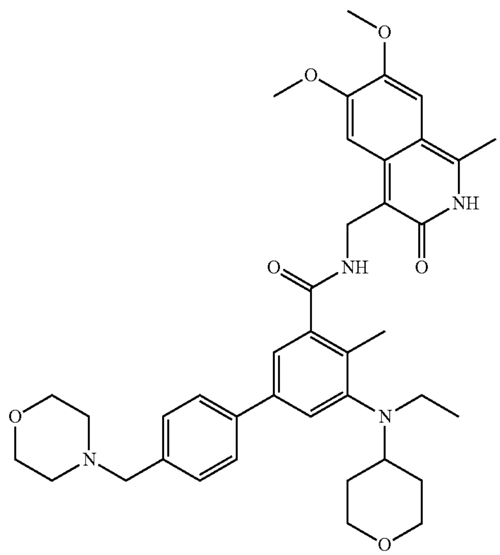 [SMILES: CCN(c1cc(-c2ccc(CN3CCOCC3)cc2)cc(C(=O)NCc2c(=O)[nH]c(C)c3cc(OC)c(OC)cc23)c1C)C1CCOCC1] | N-((6,7-Dimethoxy-1-methyl-3-oxo-2,3-dihydroisoquinolin-4-yl)methyl)-5-(ethyl(tetrahydro-2H-pyran-4-yl)amino)-4-methyl-4'-(morpholinomethyl)-[1,1'-biphenyl]-3-carboxamide | 669.3 |
| 4 | 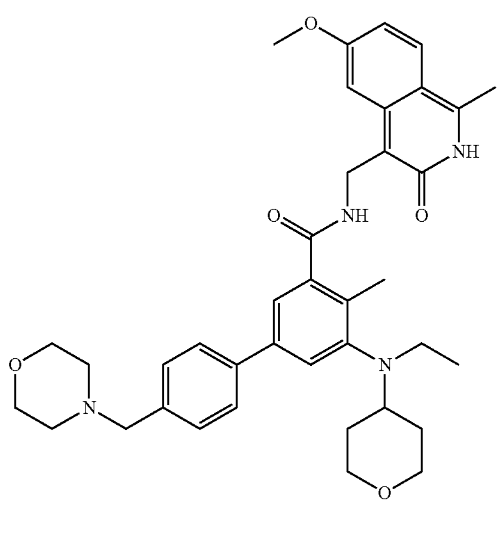 [SMILES: CCN(c1cc(-c2ccc(CN3CCOCC3)cc2)cc(C(=O)NCc2c(=O)[nH]c(C)c3ccc(OC)cc23)c1C)C1CCOCC1] | 5-(Ethyl(tetrahydro-2H-pyran-4-yl)amino)-N-((6-methoxy-1-methyl-3-oxo-2,3-dihydroisoquinolin-4-yl)methyl)-4-methyl-4'-(morpholinomethyl)-[1,1'-biphenyl]-3-carboxamide | 639.8 |

| Ex. No. | Structure | Name | LCMS (M + H) |
|---|---|---|---|
| 5 | 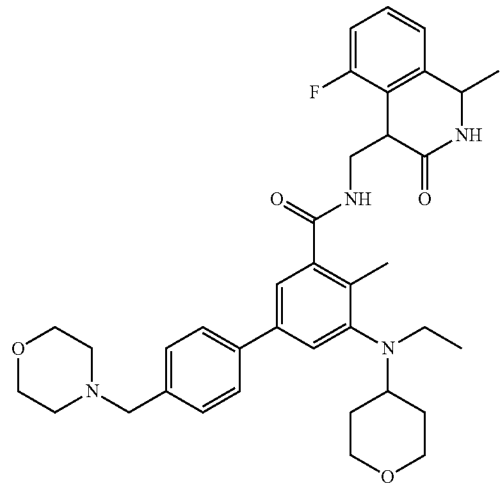 [SMILES: CCN(c1cc(-c2ccc(CN3CCOCC3)cc2)cc(C(=O)NCC2C(=O)NC(C)c3cccc(F)c32)c1C)C1CCOCC1] | 5-(Ethyl(tetrahydro-2H-pyran-4-yl)amino)-N-((5-fluoro-1-methyl-3-oxo-1,2,3,4-tetrahydroisoquinolin-4-yl)methyl)-4-methyl-4'-(morpholinomethyl)-[1,1'-biphenyl]-3-carboxamide | 629.7 |
| 6 | 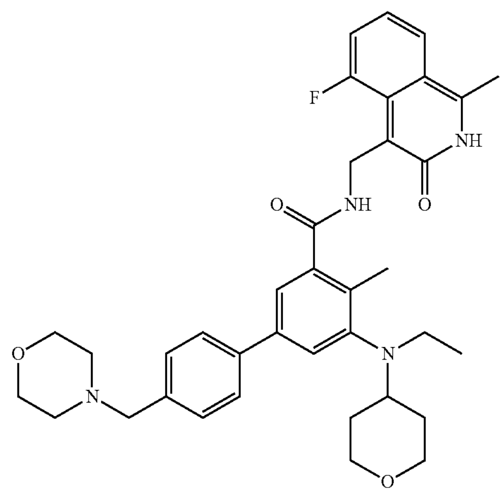 [SMILES: CCN(c1cc(-c2ccc(CN3CCOCC3)cc2)cc(C(=O)NCc2c(=O)[nH]c(C)c3cccc(F)c23)c1C)C1CCOCC1] | 5-(Ethyl(tetrahydro-2H-pyran-4-yl)amino)-N-((5-fluoro-1-methyl-3-oxo-2,3-dihydroisoquinolin-4-yl)methyl)-4-methyl-4'-(morpholinomethyl)-[1,1'-biphenyl]-3-carboxamide | 627.3 |
| 7 | 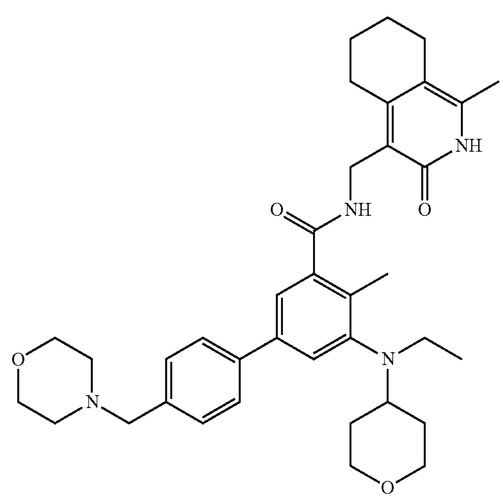 [SMILES: CCN(c1cc(-c2ccc(CN3CCOCC3)cc2)cc(C(=O)NCc2c3c(c(C)[nH]c2=O)CCCC3)c1C)C1CCOCC1] | 5-(Ethyl(tetrahydro-2H-pyran-4-yl)amino)-4-methyl-N-((1-methyl-3-oxo-2,3,5,6,7,8-hexahydroisoquinolin-4-yl)methyl)-4'-(morpholinomethyl)-[1,1'-biphenyl]-3-carboxamide | 613.4 |

-continued

| Ex. No. | Structure | Name | LCMS (M + H) |
|---|---|---|---|
| 8 | 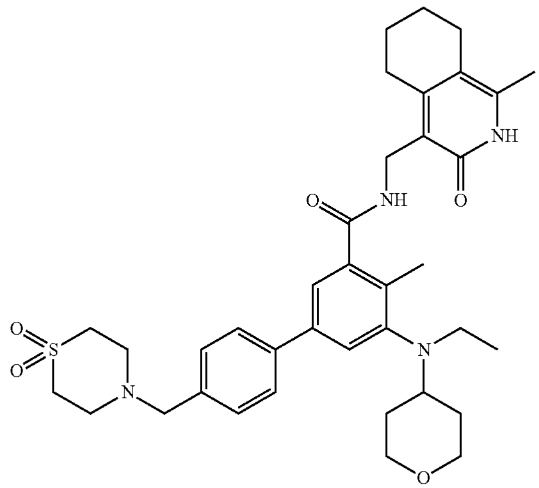 [SMILES: CCN(c1cc(-c2ccc(CN3CCS(=O)(=O)CC3)cc2)cc(C(=O)NCc2c3c(c(C)[nH]c2=O)CCCC3)c1C)C1CCOCC1] | 4'-((1,1-Dioxidothiomorpholino)methyl)-5-(ethyl(tetrahydro-2H-pyran-4-yl)amino)-4-methyl-N-((1-methyl-3-oxo-2,3,5,6,7,8-hexahydroisoquinolin-4-yl)methyl)-[1,1'-biphenyl]-3-carboxamide | 661.7 |
| 9 | 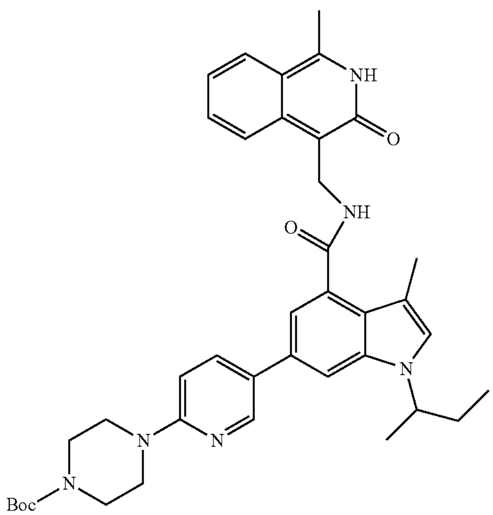 [SMILES: CCC(C)n1cc(C)c2c(C(=O)NCc3c(=O)[nH]c(C)c4ccccc34)cc(-c3ccc(N4CCN(C(=O)OC(C)(C)C)CC4)nc3)cc21] | tert-Butyl 4-(5-(1-(sec-butyl)-3-methyl-4-(((1-methyl-3-oxo-2,3-dihydroisoquinolin-4-yl)methyl)carbamoyl)-1H-indol-6-yl)pyridin-2-yl)piperazine-1-carboxylate | 663.3 |
| 10 | 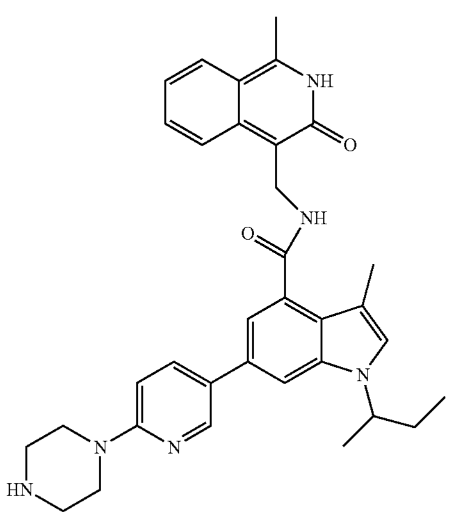 [SMILES: CCC(C)n1cc(C)c2c(C(=O)NCc3c(=O)[nH]c(C)c4ccccc34)cc(-c3ccc(N4CCNCC4)nc3)cc21] | 1-(sec-Butyl)-3-methyl-N-((1-methyl-3-oxo-2,3-dihydroisoquinolin-4-yl)methyl)-6-(6-(piperazin-1-yl)pyridin-3-yl)-1H-indole-4-carboxamide | 563.3 |

-continued

| Ex. No. | Structure | Name | LCMS (M + H) |
|---|---|---|---|
| 11 | 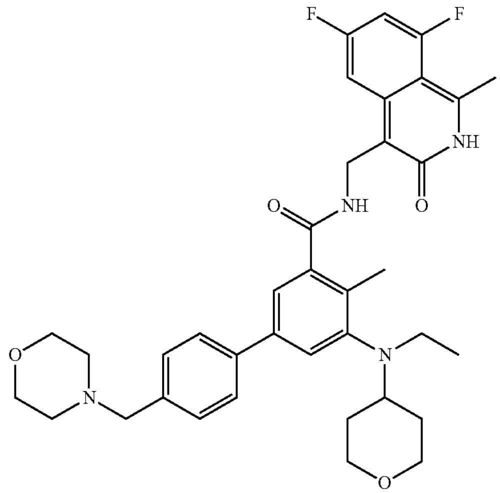 [SMILES: CCN(c1cc(-c2ccc(CN3CCOCC3)cc2)cc(C(=O)NCc2c(=O)[nH]c(C)c3c(F)cc(F)cc23)c1C)C1CCOCC1] | N-((6,8-Difluoro-1-methyl-3-oxo-2,3-dihydroisoquinolin-4-yl)methyl)-5-(ethyl(tetrahydro-2H-pyran-4-yl)amino)-4-methyl-4'-(morpholinomethyl)-[1,1'-biphenyl]-3-carboxamide | 645.5 |
| 12 | 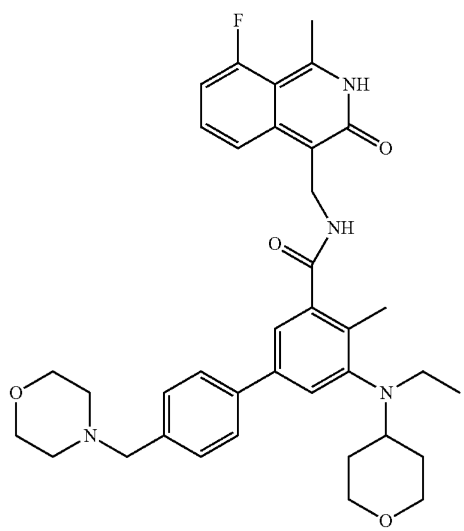 [SMILES: CCN(c1cc(-c2ccc(CN3CCOCC3)cc2)cc(C(=O)NCc2c(=O)[nH]c(C)c3c(F)cccc23)c1C)C1CCOCC1] | 5-(Ethyl(tetrahydro-2H-pyran-4-yl)amino)-N-((8-fluoro-1-methyl-3-oxo-2,3-dihydroisoquinolin-4-yl)methyl)-4-methyl-4'-(morpholinomethyl)-[1,1'-biphenyl]-3-carboxamide | 627.4 |
| 13 | 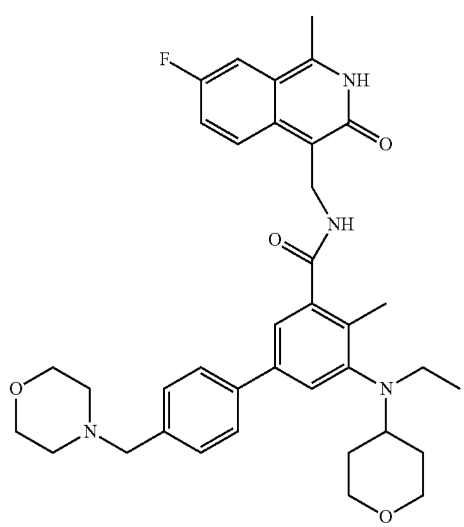 [SMILES: CCN(c1cc(-c2ccc(CN3CCOCC3)cc2)cc(C(=O)NCc2c(=O)[nH]c(C)c3cc(F)ccc23)c1C)C1CCOCC1] | 5-(Ethyl(tetrahydro-2H-pyran-4-yl)amino)-4-methyl-N-((1-methyl-3-oxo-7-(trifluoromethyl)-2,3-dihydroisoquinolin-4-yl)methyl)-4'-(morpholinomethyl)-[1,1'-biphenyl]-3-carboxamide | 677.5 |

-continued

| Ex. No. | Structure | Name | LCMS (M + H) |
|---|---|---|---|
| 14 | 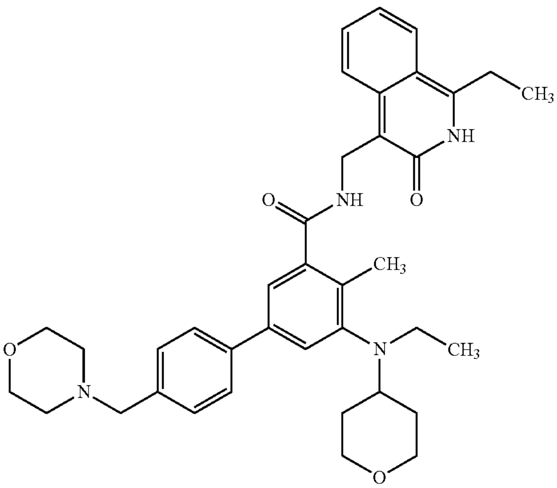 [SMILES: CCc1[nH]c(=O)c(CNC(=O)c2cc(-c3ccc(CN4CCOCC4)cc3)cc(N(CC)C3CCOCC3)c2C)c2ccccc12] | 5-(Ethyl(tetrahydro-2H-pyran-4-yl)amino)-N-((1-ethyl-3-oxo-2,3-dihydroisoquinolin-4-yl)methyl)-4-methyl-4'-(morpholinomethyl)-[1,1'-biphenyl]-3-carboxamide | 623.5 |
| 15 | 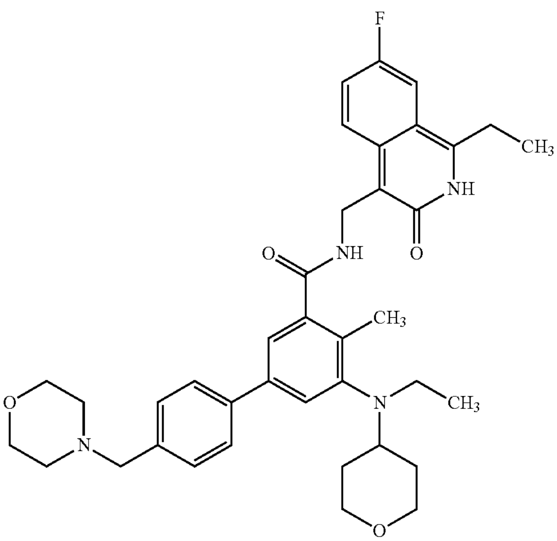 [SMILES: CCc1[nH]c(=O)c(CNC(=O)c2cc(-c3ccc(CN4CCOCC4)cc3)cc(N(CC)C3CCOCC3)c2C)c2ccc(F)cc12] | 5-(Ethyl(tetrahydro-2H-pyran-4-yl)amino)-N-((1-ethyl-7-fluoro-3-oxo-2,3-dihydroisoquinolin-4-yl)methyl)-4-methyl-4'-(morpholinomethyl)-[1,1'-biphenyl]-3-carboxamide | 641.5 |
| 16 | 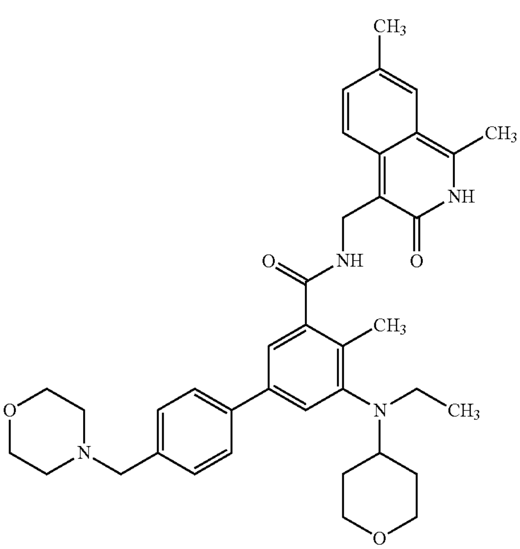 [SMILES: CCN(c1cc(-c2ccc(CN3CCOCC3)cc2)cc(C(=O)NCc2c(=O)[nH]c(C)c3cc(C)ccc23)c1C)C1CCOCC1] | N-((1,7-Dimethyl-3-oxo-2,3-dihydroisoquinolin-4-yl)methyl)-5-(ethyl(tetrahydro-2H-pyran-4-yl)amino)-4-methyl-4'-(morpholinomethyl)-[1,1'-biphenyl]-3-carboxamide | 623.4 |

| Ex. No. | Structure | Name | LCMS (M + H) |
|---|---|---|---|
| 17 | 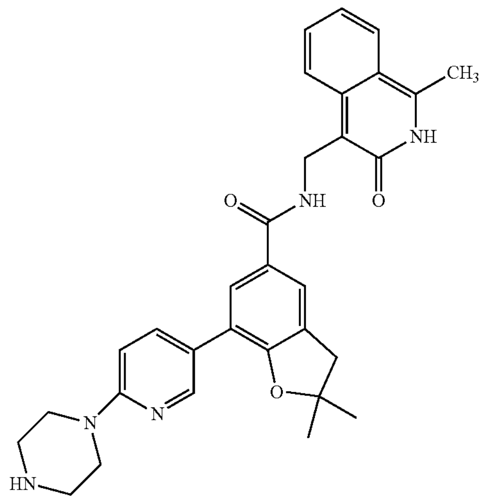 [SMILES: Cc1[nH]c(=O)c(CNC(=O)c2cc3c(c(-c4ccc(N5CCNCC5)nc4)c2)OC(C)(C)C3)c2ccccc12] | 2,2-Dimethyl-N-((1-methyl-3-oxo-2,3-dihydroisoquinolin-4-yl)methyl)-7-(6-(piperazin-1-yl)pyridin-3-yl)-2,3-dihydrobenzofuran-5-carboxamide | 524.3 |

Biological Assay

EZH2 Histone Methyl Transferase Assay

The effectiveness of compounds of the present invention as inhibitors of hitone methyl transferases can be readily tested by assays known to those skilled in the art. For example, in vitro histone methyl transferase assays may be conducted with a relevant purified histone methyl transferase and an appropriate synthetic substrate to determine the inhibitory activity of the compounds. Assays for inhibition of EZH2 by the instant compounds were performed in 384-well plates with reaction mixtures containing 350 nM of histone peptide substrate (ATKAAR-K(Me2)-SAPATG-GVKKPHRYRPG-GK(Biotin), 500 nM S-[methyl-$^3$H]adenosyl-L-methionine (55-85 Ci/mmol), 50 mM Tris-HCl (pH 9.0), 50 mM NaCl, 1 mM dithiothreitol, Tween-20 at 0.01% and fatty-acid free bovine serum albumin at 0.01%, and recombinant EZH2-641F complex (EZH2 Y641F/EED/SUZ12/RbAp48/AEBP2) at 5 nM (≥98% purity, BPS Bioscience) or 15 nM (50% purity, in-house). Reaction mixtures were incubated at room temperature for 3 hours, and the reactions were terminated by 0.005% poly-L-lysine solution in 20 mM Tris-HCl (pH 7.5) and 150 mM NaCl. Reaction products were captured by binding to strepavidin-conjugated imaging beads. Incorporation of radioactive methyl group into the histone peptide substrate was determined in Leadseeker (GE Healthcare) by means of scintiallation proximity assay. Dose response curves were generated to determine the concentration required to inhibit 50% of methyl transferase activity ($EC_{50}$). Compounds were dissolved at 10 mM in dimethylsulfoxide (DMSO) and evaluated at eleven concentrations. $EC_{50}$ values were derived by non-linear regression analysis. Compounds with an EC50≤5.0 μM are shown with (+), compounds with an EC50≤0.5 μM are shown with (++) and those with an EC50≤0.05 μM are shown with (+++).

| Example No. | EZH2 $EC_{50}$ (μM) |
|---|---|
| 1 | +++ |
| 2 | +++ |
| 3 | + |
| 4 | + |
| 5 | + |
| 6 | +++ |
| 7 | ++ |
| 8 | ++ |
| 9 | + |
| 10 | ++ |
| 11 | + |
| 12 | + |
| 13 | ++ |
| 14 | ++ |
| 15 | +++ |
| 16 | +++ |
| 17 | + |

The invention claimed is:

1. The compound which is 5-(Ethyl(tetrahydro-2H-pyran-4-yl)amino)-4-methyl-N-((1-methyl-3-oxo-2,3-dihydroisoquinolin-4-yl)methyl)-4'-(morpholinomethyl)-[1,1'-biphenyl]-3-carboxamide, 5-(Ethyl(tetrahydro-2H-pyran-4-yl)amino)-N-((7-fluoro-1-methyl-3-oxo-2,3-dihydroisoquinolin-4-yl)methyl)-4-methyl-4'-(morpholinomethyl)-[1,1'-biphenyl]-3-carboxamide, N-((6,7-Dimethoxy-1-methyl-3-oxo-2,3-dihydroisoquinolin-4-yl)methyl)-5-(ethyl(tetrahydro-2H-pyran-4-yl)amino)-4-methyl-4'-(morpholinomethyl)-[1,1'-biphenyl]-3-carboxamide, 5-(Ethyl(tetrahydro-2H-pyran-4-yl)amino)-N-((6-methoxy-1-methyl-3-oxo-2,3-dihydroisoquinolin-4-yl)methyl)-4-methyl-4'-(morpholinomethyl)-[1,1'-biphenyl]-3-carboxamide, 5-(Ethyl(tetrahydro-2H-pyran-4-yl)amino)-N-((5-fluoro-1-methyl-3-oxo-1,2,3,4-tetrahydroisoquinolin-4-yl)methyl)-4-methyl-4'-(morpholinomethyl)-[1,1'-biphenyl]-3-carboxamide, 5-(Ethyl(tetrahydro-2H-pyran-4-yl)amino)-N-((5-fluoro-1-methyl-3-oxo-2,3-dihydroisoquinolin-4-yl)methyl)-4-methyl-4'-(morpholinomethyl)-[1,1'-biphenyl]-3-carboxamide, tert-Butyl 4-(5-(1-(sec-butyl)-3-methyl-4-(((1-methyl-3-oxo-2,3-dihydroisoquinolin-4-yl)methyl)carbamoyl)-1H-indo-6-yl)pyridin-2-yl)piperazine-1-carboxylate, 1-(sec-Butyl)-3-methyl-N-((1-methyl-3-oxo-2,3-dihydroisoquinolin-4-yl)methyl)-6-(6-(piperazin-1-yl)pyridin-3-yl)-1H-indole-4-carboxamide, N-((6,8-Difluoro-1-methyl-3-oxo-2,3-dihydroisoquinolin-4-yl)methyl)-5-(ethyl(tetrahydro-2H-pyran-4-yl)amino)-4-methyl-4'-(morpholinomethyl)-[1,1'-biphenyl]-3-carboxamide, 5-(Ethyl(tetrahydro-2H-pyran-4-yl)amino)-N-((8-fluoro-1-methyl-3-oxo-2,3-dihydroisoquinolin-4-yl)methyl)-4-methyl-4'-(morpholinomethyl)-[1,1'-biphenyl]-3-carboxamide, 5-(Ethyl(tetrahydro-2H-pyran-4-yl)amino)-4-methyl-N-((1-methyl-3-oxo-7-(trifluoromethyl)-2,3-dihydroisoquinolin-4-yl)methyl)-4'-(morpholinomethyl)-[1,1'-biphenyl]-3-carboxamide, 5-(Ethyl(tetrahydro-2H-pyran-4-yl)amino)-N-((1-ethyl-3-oxo-2,3-dihydroisoquinolin-4-yl)methyl)-4-methyl-4'-(morpholinomethyl)-[1,1'-biphenyl]-3-carboxamide, 5-(Ethyl(tetrahydro-2H-pyran-4-yl)amino)-N-((1-ethyl-7-fluoro-3-oxo-2,3-dihydroisoquinolin-4-yl)methyl)-4-methyl-4'-(morpholinomethyl)-[1,1'-biphenyl]-3-carboxamide, N-((1,7-Dimethyl-3-oxo-2,3-dihydroisoquinolin-4-yl)methyl)-5-(ethyl(tetrahydro-2H-pyran-4-yl)amino)-4-methyl-4'-(morpholinomethyl)-[1,1'-biphenyl]-3-carboxamide, 2,2-Dimethyl-N-((1-methyl-3-oxo-2,3-dihydroisoquinolin-4-yl)methyl)-7-(6-(piperazin-1-yl)pyridin-3-yl)-2,3-dihydrobenzofuran-5-carboxamide, or a pharmaceutically acceptable salt, tautomer or stereoisomer thereof.

2. A pharmaceutical composition comprising one or more compounds according to claim 1 and a pharmaceutically acceptable carrier or diluent.

\* \* \* \* \*